United States Patent
Hobman et al.

(10) Patent No.: US 11,807,906 B2
(45) Date of Patent: Nov. 7, 2023

(54) PEROXISOME BIOMARKERS IN HIV DISEASE PROGRESSION AND PEROXISOME ACTIVATING DRUGS FOR HIV TREATMENT

(71) Applicant: THE GOVERNORS OF THE UNIVERSITY OF ALBERTA, Edmonton (CA)

(72) Inventors: Tom C. Hobman, Edmonton (CA); Chris Power, Edmonton (CA); Zaikun Xu, Edmonton (CA)

(*) Notice: Subject to any disclaimer, the term of this patent is extended or adjusted under 35 U.S.C. 154(b) by 493 days.

(21) Appl. No.: 16/606,665

(22) PCT Filed: May 7, 2018

(86) PCT No.: PCT/CA2018/050541
§ 371 (c)(1),
(2) Date: Oct. 18, 2019

(87) PCT Pub. No.: WO2018/205016
PCT Pub. Date: Nov. 15, 2018

(65) Prior Publication Data
US 2020/0340056 A1 Oct. 29, 2020

Related U.S. Application Data

(60) Provisional application No. 62/503,182, filed on May 8, 2017.

(51) Int. Cl.
| | | |
|---|---|---|
| C12Q 1/68 | (2018.01) | |
| C12Q 1/6883 | (2018.01) | |
| A61P 31/18 | (2006.01) | |
| A61K 31/167 | (2006.01) | |

(52) U.S. Cl.
CPC .......... *C12Q 1/6883* (2013.01); *A61K 31/167* (2013.01); *A61P 31/18* (2018.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2008/0286260 A1 | 11/2008 | Golz et al. |
| 2012/0015966 A1 | 1/2012 | Lin et al. |

FOREIGN PATENT DOCUMENTS

| | | |
|---|---|---|
| CN | 1300829 | 6/2001 |
| CN | 1345831 | 4/2002 |
| CN | 1333343 | 1/2020 |

OTHER PUBLICATIONS

Osman et al., "Molecular recognition of long chain fatty acids by peroxisome proliferator-activated receptor a", (2009) Med Chem Res 18: 8-19 (Year: 2009).*
Kihara, "Very long-chain fatty acids: elongation, physiology and related disorders",(2012) J Biochem 152(5): pp. 387 (Year: 2012).*
Smith et al., "Peroxisomes take shape", (2013) Nat Rev: Molecular Cell Biol. 14: 803-817 (Year: 2013).*
Sexton et al., "High content screening for nonclassical peroxisome proliferators", (2010) Int J High Throughput Screen 2010(1): 127-140 (Year: 2010).*
Reddy et al., "Hepatic Peroxisome Proliferation: Induction by Two Novel Compounds Structurally Unrelated to Clofibrate", (1975) Science 190(4216):787-789 (Year: 1975).*
Asahchop et al., (2016) "Plasma microRNA profiling predicts HIV-associated neurocognitive disorder", AIDS, 30(13)(24):2021-2031.
Lodhi et al., (2014) "Peroxisomes: a nexus for lipid metabolism and cellular signaling.", Cell Metabolism, (19)3:380-392.
Nordgren et al., (2013) "Peroxisome degradation in mammals: mechanisms of action, rencet advances, and perspectives.", Frontiers in Physiology, 4:145.
Potula et al., (2008) "Peroxisome proliferator-activated receptor-gamma activation suppresses HIV-1replication in an animal model of encephalitis.", Aids, 22(13):1539-1549.
Shores et al., (2015) "Hepatic peroxisome proliferator-activated receptor y and a-mRNA expression in HCV-infected adults is decreased by HIV co-infection and is also affected by ethnicity.", Clinics, (12):790-796.
Skolnik et al., (2002) "Stimulation of Peroxisome Proliferator-Activated Receptors a and y Blocks HIV-1 Replication and TNFa Production in Acutely Infected Primary Blood Cells, Chronically Infected UI Cells, and Alveolar MAcrophages From HIV-Infected Subjects", Journal of Acquired Immune Deficiency Syndromes, 31(1):1-10.
Wong et al., (2008) "Targeted Elimination of Peroxisomes During Viral Infection: Lessons from HIV and Other Viruses.", DNA Cell Bioi., 37(5):417-421.
Xu et al., (2017) "MicroRNAs upregulated during HIV infection target peroxisome biogenesis factors: Implications for virus biology, disease mechanisms and neuropathology", PLOS Pathogens, 1-29.

* cited by examiner

*Primary Examiner* — Jehanne S Sitton
(74) *Attorney, Agent, or Firm* — Bennett Jones LLP

(57) ABSTRACT

The present disclosure provides methods for assessing likelihood of development of HIV-associated neurocognitive disorder (HAND) in a HIV patient. Also provided herein are methods for treating a HIV patient, such as, a HIV patient with increased level of a mi RNA that downregulates a peroxin and/or decreased level of a peroxisomal activity biomarker and/or increased level of a substrate of a peroxisomal enzyme. The present disclosure also provides methods for monitoring efficacy of a treatment regimen for a HIV patient.

4 Claims, 22 Drawing Sheets

Specification includes a Sequence Listing.

FIG. 10
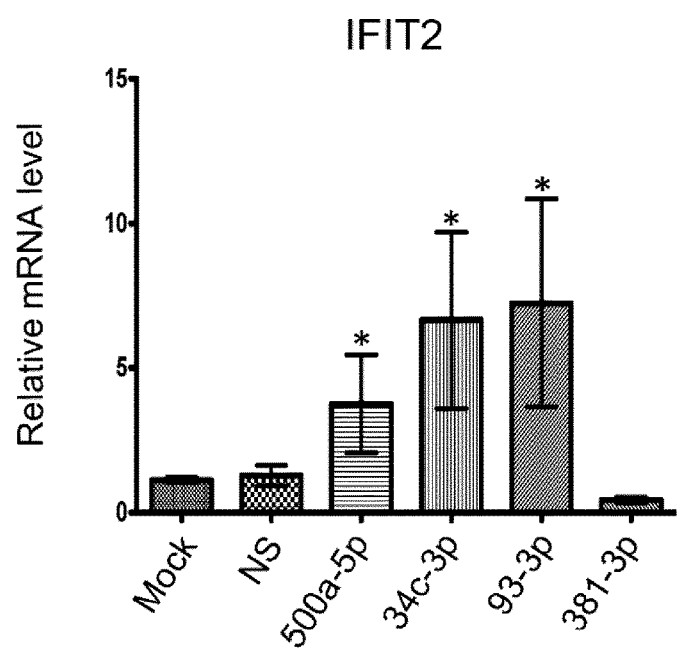
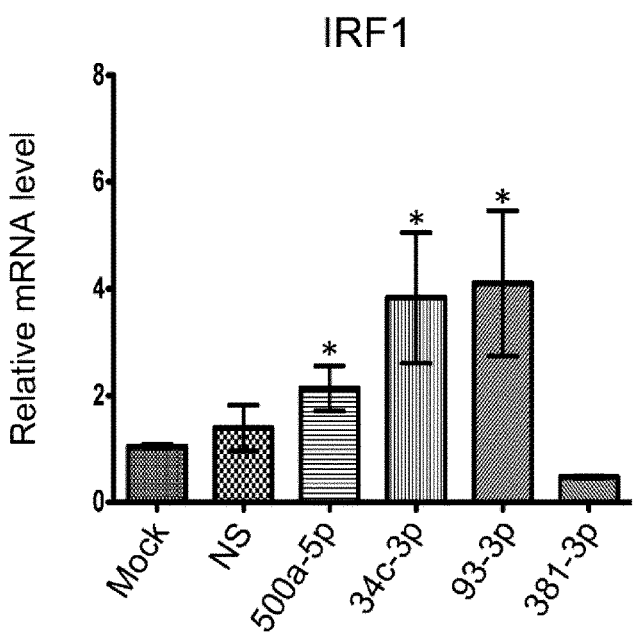

FIG. 15A

| miRNA name | Predicted targets (by at least two algorithms) | |
|---|---|---|
| hsa-miR-4685-5p | NDOR1 | PEX14 |
| | VDR | TAL1 |
| | PPP3CB | FURIN |
| | NRAS | PRKCA |
| | IRF1 | TK2 |
| | MAVS | BCL2 |
| hsa-miR-4655-5p | KSR1 | AKAP7 |
| hsa-miR-483-5p | ALCAM | MAPK3 |
| hsa-miR-4732-5p | BCLAF1 | MKRN3 |
| | CPSF6 | DHX57 |
| | CXCL10 | DHX38 |
| | GRM5 | |
| hsa-miR-4739 | NFAT5 | MYOM1 |
| | KSR2 | MARK2 |
| | CADM3 | VAPB |
| | BAK1 | IL6R |
| | NCAN | DAPK1 |
| | DDX17 | CXCR3 |
| | DHX15 | NLGN3 |
| | SYT2 | STAT2 |
| | OCLN | CD4 |

FIG. 15B

| miRNA name | Predicted targets (by at least two algorithms) | |
|---|---|---|
| hsa-miR-381 | TAOK1　MAVS　CLDN1　ITCH　DDX6　KRAS　VAPA　PEX13　MARK1　NFIA　NFIB　TEK　PCSK2 | CXCL3　XPO7　STAT1　DHX33　DDX52　IL13　CHEK1　CXCR4　GRM5　DHX40　TTBK2　NLGN1 |
| hsa-miR-200c-3p | NFIA　MAP4K5　NLGN4X　DDX3X　DDX3Y　DDX1　DDX53　DDX55　VAPA　TAOK3　JUN　PCSK2 | MAP3K1　CXCL9　MAP4K3　DCP2　IRF4　TBK1　NUP153　MMP16　XPO1　IPO7　NOTCH1 |
| hsa-miR-181a-2-3p | TAOK1　TAOK3　DDX46 | MAPK8　NFAT5 |

| miRNA name | Predicted targets (by at least two algorithms) | |
|---|---|---|
| hsa-miR-1271 | MTSS1　MSN　KRAS　RAB8B　MAP2K1　IRF6　NLGN2　AK3 | MED1　BCL2　TTBK2　TAOK1　LNX2　PRKCE　CASP2　MRAS |
| hsa-miR-770-5p | MYO6　NTRK2　MARK1 | MAP3K1　DHX15　VAPA |
| hsa-miR-767-5p | NFIA　NRAS　SCAI　DDX5　DDX3X　CLDN11　VAPA | FURIN　OCLN　TAOK2　XPO4　MARK1　KRAS |
| hsa-miR-589-3p | MMP16　CCR9　AAK1 | DHX36　MAP3K7　VAPB |
| hsa-miR-500a-5p | IPO9　PEX2　MMP8　MMP16 | PAPKAPK3　TIA1　CADM2　CCR4 |
| hsa-miR-106b-2-3p | IRAK2 | |
| hsa-miR-93-3p | IRF1　IRF2　FURIN　DAPK1　NFIA　NLGN1　DDX26　PTEN | DDX5　STAT3　XPO4　CLDN8　PEX11B　CD58　MAVS　NFAT5 |
| hsa-miR-34c-3p | NCKAP1　MAP3K2　SCAI　PEX7　MARK1 | DHX35　DHX9　EIF4E　MMP24 |
| hsa-miR-23b-5p | ADAM10　IL6R　CXCL12　LAMP1　IRF1　IRF2 | DHX15　TLR4　KSR1　DDX6　DDX5　CADM3 |

FIG. 16

| Primer name | Sequence |
|---|---|
| PEX2/3'-UTR-Forward | 5-CTATAAGCTTAAACTAAAATTGCTTCCTTTGAGG-3 |
| PEX2/3'-UTR-Reverse | 5-GCGTAAGCTTGATTATGCACTGCTGTTACT-3 |
| PEX7/3'-UTR-Forward | 5-CTATAAGCTTCTGGGACTACAGTTTTCACCA-3 |
| PEX7/3'-UTR-Reverse | 5-GCGTAAGCTTATTTATCACAGCAGTGATTAT-3 |
| PEX11B/3'-UTR-Forward | 5-CTATAAGCTTCCTTCCGGTACAGGATAAG-3 |
| PEX11B/3'-UTR-Reverse | 5-GCGTAAGCTTGTCGATGAGCAAACTGAACTT-3 |
| PEX13/3'-UTR-Forward | 5-CTATAAGCTTTATCTTTCATGTTTGCCTGC-3 |
| PEX13/3'-UTR-Reverse | 5-GCGTAAGCTTCAGATCAGAAAATTTTATTATTGAG-3 |
| miR-500a-5p-Forward | 5-TAATCCTTGCTACCTGGGTGAGA-3 |
| miR-34c-3p-Forward | 5-AATCACTAACCACACGGCCAGG-3 |
| miR-93-3p-Forward | 5-ACTGCTGAGCTAGCACTTCCCG-3 |
| miR-381-3p-Forward | 5-TATACAAGGGCAAGCTCTCTGT-3 |
| miR-483-5p-Forward | 5-AAGACGGGAGGAAAGAAGGGAG-3 |
| Viperin-Forward | 5-TGGTGAGGTTCTGCAAAGTAG-3 |
| Viperin-Reverse | 5-GTCACAGGAGATAGCGAGAATG-3 |
| IRF1-Forward | 5-CATGGCTGGGACATCAACAA-3 |
| IRF1-Reverse | 5-GTTCATGGCACAGCGAAAGTT-3 |
| IFI6-Forward | 5-GGTCTGCGATCCTGAATGGG-3 |
| IFI6-Reverse | 5-TCACTATCGAGATACTTGTGGGT-3 |
| IFIT2-Forward | 5-AGAAGCAGGCAATCACAGAAAA-3 |
| IFIT2-Reverse | 5-CTGAAACCGACCATAGTGGAAAT-3 |
| OAS1-Forward | 5-TGTCCCTCTCTAAATGCTGCTC-3 |
| OAS1-Reverse | 5-GGAAGCAGGAGGTCTCACCAG-3 |

FIG. 17
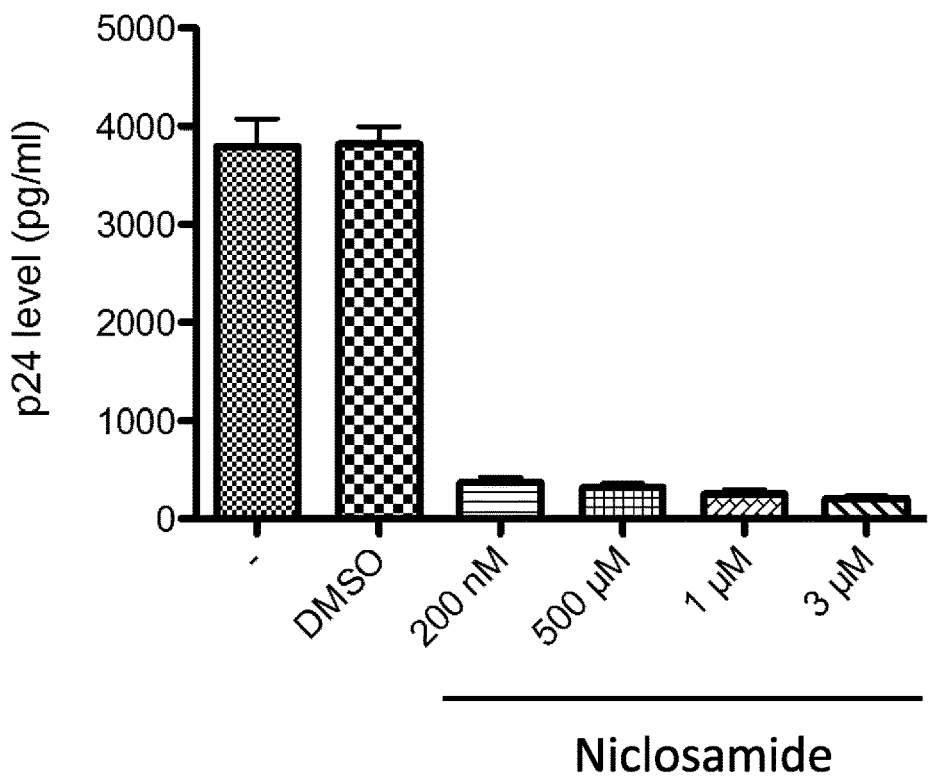
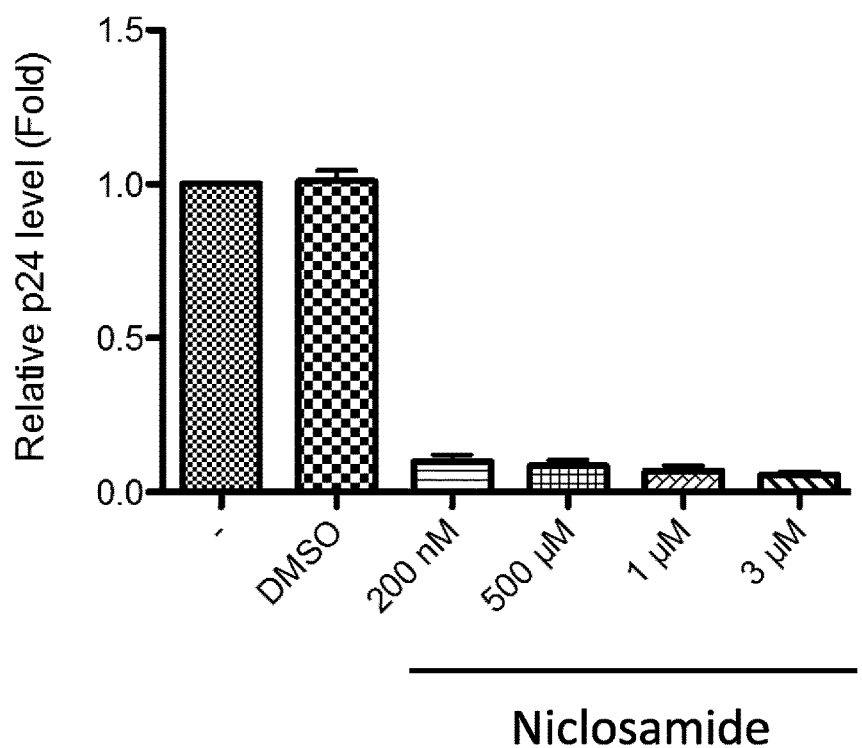

SEQUENCE LISTING

<160> NUMBER OF SEQ ID NOS: 23

<210> SEQ ID NO 1
<211> LENGTH: 34
<212> TYPE: DNA
<213> ORGANISM: Artificial sequence
<220> FEATURE:
<223> OTHER INFORMATION: synthetic polynucleotide

<400> SEQUENCE: 1
ctataagctt aaactaaaat tgcttccttt gagg                          34

<210> SEQ ID NO 2
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 2
gcgtaagctt gattatgcac tgctgttact                               30

<210> SEQ ID NO 3
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 3
ctataagctt ctgggactac agttttcacc a                             31

<210> SEQ ID NO 4
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 4
gcgtaagctt atttatcaca gcagtgatta t                             31

<210> SEQ ID NO 5
<211> LENGTH: 29
<212> TYPE: DNA
<213> ORGANISM: Artificial sequence
<220> FEATURE:
<223> OTHER INFORMATION: synthetic polynucleotide

<400> SEQUENCE: 5
ctataagctt ccttccggta caggataag                                29

<210> SEQ ID NO 6
<211> LENGTH: 31
<212> TYPE: DNA
<213> ORGANISM: Artificial sequence
<220> FEATURE:
<223> OTHER INFORMATION: synthetic polynucleotide

<400> SEQUENCE: 6
gcgtaagctt gtcgatgagc aaactgaact t                             31

<210> SEQ ID NO 7
<211> LENGTH: 30
<212> TYPE: DNA
<213> ORGANISM: Artificial sequence
<220> FEATURE:
<223> OTHER INFORMATION: synthetic polynucleotide

<400> SEQUENCE: 7
ctataagctt tatctttcat gtttgcctgc                                              30

<210> SEQ ID NO 8
<211> LENGTH: 35
<212> TYPE: DNA
<213> ORGANISM: Artificial sequence
<220> FEATURE:
<223> OTHER INFORMATION: synthetic polynucleotide

<400> SEQUENCE: 8
gcgtaagctt cagatcagaa aattttatta ttgag                                        35

<210> SEQ ID NO 9
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 9
taatccttgc tacctgggtg aga                                                     23

<210> SEQ ID NO 10
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 10
aatcactaac cacacggcca gg                                                      22

<210> SEQ ID NO 11
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 11
actgctgagc tagcacttcc cg                                                      22

<210> SEQ ID NO 12
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 12
tatacaaggg caagctctct gt                                                      22

<210> SEQ ID NO 13
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 13
aagacgggag gaaagaaggg ag                                                      22

```
<210> SEQ ID NO 14
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 14
tggtgaggtt ctgcaaagta g                                         21

<210> SEQ ID NO 15
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 15
gtcacaggag atagcgagaa tg                                        22

<210> SEQ ID NO 16
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 16
catggctggg acatcaacaa                                           20

<210> SEQ ID NO 17
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 17
gttcatggca cagcgaaagt t                                         21

<210> SEQ ID NO 18
<211> LENGTH: 20
<212> TYPE: DNA
<213> ORGANISM: Artificial sequence
<220> FEATURE:
<223> OTHER INFORMATION: synthetic polynucleotide

<400> SEQUENCE: 18
ggtctgcgat cctgaatggg                                           20

<210> SEQ ID NO 19
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 19
tcactatcga gatacttgtg ggt                                       23

<210> SEQ ID NO 20
<211> LENGTH: 22
<212> TYPE: DNA
<213> ORGANISM: Artificial sequence
<220> FEATURE:
<223> OTHER INFORMATION: synthetic polynucleotide
```

```
<400> SEQUENCE: 20
agaagcaggc aatcacagaa aa                                              22

<210> SEQ ID NO 21
<211> LENGTH: 23
<212> TYPE: DNA
<213> ORGANISM: Artificial sequence
<220> FEATURE:
<223> OTHER INFORMATION: synthetic polynucleotide

<400> SEQUENCE: 21
ctgaaaccga ccatagtgga aat                                             23

<210> SEQ ID NO 22
<211> LENGTH: 22
<212> TYPE: DNA
<213> ORGANISM: Artificial sequence
<220> FEATURE:
<223> OTHER INFORMATION: synthetic polynucleotide

<400> SEQUENCE: 22
tgtccctctc taaatgctgc tc                                              22

<210> SEQ ID NO 23
<211> LENGTH: 21
<212> TYPE: DNA
<213> ORGANISM: Artificial sequence
<220> FEATURE:
<223> OTHER INFORMATION: synthetic polynucleotide

<400> SEQUENCE: 23
ggaagcagga ggtctcacca g                                               21
```

PEROXISOME BIOMARKERS IN HIV DISEASE PROGRESSION AND PEROXISOME ACTIVATING DRUGS FOR HIV TREATMENT

CROSS-REFERENCE

This application claims the benefit of U.S. Provisional Patent Application No. 62/503,182, filed May 8, 2017, which application is incorporated herein by reference in its entirety.

INCORPORATION BY REFERENCE OF SEQUENCE LISTING

A Sequence Listing is provided herewith as a text file, "81436-171.pct.seqlist.2018MAY7.txt" created on May 4, 2018 and having a size of 5 KB. The contents of the text file are incorporated by reference herein in their entirety.

INTRODUCTION

HIV-associated neurocognitive disorders (HAND) represent a spectrum neurological syndrome that affects up to 25% of patients with HIV/AIDS. Multiple pathogenic mechanisms contribute to the development of HAND symptoms of which include chronic neuroinflammation and eventual neurodegeneration.

There is a need for biomarkers that can predict development of HAND to facilitate identification and treatment of at risk patients.

SUMMARY

The present disclosure provides methods of assessing likelihood of development of HIV-associated neurocognitive disorder (HAND) in a HIV patient. Also provided herein are methods for treating a HIV patient, such as, a HIV patient with increased level of a miRNA that downregulates a peroxin and/or decreased level of a peroxisomal activity biomarker and/or increased level of a substrate for a peroxisomal enzyme. The present disclosure also provides methods for monitoring efficacy of a treatment regimen for a HIV patient.

In certain embodiments, a method for predicting risk for development of human immunodeficiency virus (HIV)-associated neurocognitive disorder (HAND) in a HIV patient is provided. The method may include assaying in a biological sample of the HIV patient: (i) a level of a microRNA (miRNA) that downregulates expression of a peroxin, where increased levels of the miRNA is indicative of increased risk for development of HAND in the HIV patient; or (ii) a level of a peroxisomal activity biomarker, where decreased level of the peroxisomal activity biomarker is indicative of increased risk for development of HAND in the HIV patient; or (iii) level of a substrate of a peroxisomal enzyme, where increased levels of the substrate is indicative of increased risk for development of HAND in the HIV patient.

In certain aspects, the method may include assaying in the biological sample of the HIV patient a level of the miRNA, where the miRNA is selected from the group consisting of miR-500a-5p, miR-34c-3p, miR-93-3p, and miR-381-3p, where increased levels of the miRNA is indicative of increased risk for development of HAND in the HIV patient. In certain aspects, the miRNA is one or more of miR-500a-5p, miR-34c-3p, miR-93-3p, and miR-381-3p.

In certain aspects, the method includes assaying in the biological sample of the HIV patient a level of a peroxisomal activity biomarker, where decreased level of the peroxisomal activity biomarker is indicative of increased risk for development of HAND in the HIV patient. In certain embodiments, the peroxisomal activity biomarker may be a peroxin. In certain examples, the peroxin may be one or more of PEX2, PEX19, PEX7, PEX11B and PEX13. In another embodiment, the peroxisomal activity biomarker may be a metabolite produced by peroxisomes. In another embodiment, the peroxisomal activity biomarker may be a peroxisomal enzyme. In certain embodiments, the peroxisomal enzyme may be dihydroxyactone-phosphate acyltransferase (DHAPAT) or glutaryl-CoA oxidase.

In certain aspects, the method includes assaying in the biological sample of the HIV patient a level of a substrate for a peroxisomal enzyme, where increased level of the substrate is indicative of increased risk for development of HAND in the HIV patient. The substrate may be a long chain fatty acid comprising 14-21 carbon atoms or a very long chain fatty acid comprising 22-26 carbon atoms.

In certain cases, the biological sample is a body fluid sample, such as, a blood sample, a serum sample, a plasma sample, or a cerebrospinal fluid sample.

In certain cases, when the HIV patient has increased levels of the miRNA, the method may further include treating the HIV patient with an agent that increases peroxisome activity.

In certain cases, when the HIV patient has decreased level of the peroxisomal activity biomarker, the method further comprises treating the HIV patient with an agent that increases peroxisomal activity.

In certain cases, when the HIV patient has increased levels of the substrate for the peroxisomal enzyme, the method further comprises treating the HIV patient with an agent that increases peroxisome activity.

In certain cases, the agent may be a peroxisome proliferator-activated receptor-α (PPARα) agonist. In certain cases, the agent may be chloro-N-(2-chloro-4-nitrophenyl)-2-hydroxybenzamide (CAS No. 50-65-7) (niclosamide) or salt, solvate, clathrate, hydrate, polymorph thereof.

In certain cases, when the HIV patient does not have increased levels of the miRNA or does not have decreased level of the peroxisomal activity biomarker or does not have increased levels of the substrate for the peroxisomal enzyme, the method may further include identifying the patient as unlikely to develop HAND. In certain cases, the method may include recommending that the patient not receive treatment with an agent that increases peroxisomal activity.

In another embodiment, a method for treating a HIV patient having decreased peroxisome activity is provided. In some embodiments, the method includes administering to the HIV patient a therapeutically effective amount of an agent that increases peroxisomal activity. In certain embodiments, the administering may result in the increase in a peroxisomal activity biomarker and/or a decrease in level of a substrate of a peroxisomal enzyme. In certain cases, a method for treating a HIV patient may comprise administering to the patient a peroxisome proliferator such as chloro-N-(2-chloro-4-nitrophenyl)-2-hydroxybenzamide (CAS No. 50-65-7) (niclosamide) or salt, solvate, clathrate, hydrate, polymorph of chloro-N-(2-chloro-4-nitrophenyl)-2-hydroxybenzamide (niclosamide). In certain cases, the peroxisome proliferator may be administered in an amount effective to increase the level of peroxisomes in the patient.

In certain cases, the HIV patient may have an increased level of a microRNA (miRNA) that decreases formation of peroxisomes. In certain cases, the miRNA may be selected from the group consisting of miR-500a-5p, miR-34c-3p, miR-93-3p, and miR-381-3p.

In certain cases, the HIV patient may have a decreased level of a peroxisomal activity biomarker and/or an increased level of a substrate for the peroxisomal enzyme.

In certain cases, the HIV patient has been diagnosed as having a HIV-associated neurocognitive disorder (HAND). In certain cases, the HIV patient may have been diagnosed as having encephalitis.

In certain cases, the method includes, prior to the administering, assaying in a biological sample of the HIV patient one or more of (i) a level of a microRNA (miRNA) that downregulates expression of a peroxin; (ii) level of a peroxisomal activity biomarker; and (iii) level of a substrate for a peroxisomal enzyme.

In certain cases, the method comprises identifying the patient as likely to benefit from a treatment with an agent that increases peroxisomal activity based on assaying in a biological sample of the HIV patient one or more of (i) a level of a microRNA (miRNA) that downregulates expression of a peroxin; (ii) level of a peroxisomal activity biomarker; and (iii) level of a substrate for a peroxisomal enzyme.

In certain cases, the HIV patient does not have HAND. The biological sample may be a body fluid sample. In certain cases, the body fluid sample comprises a blood sample, a serum sample, a plasma sample, or a cerebrospinal fluid sample.

Also provided is a method for monitoring treatment of a HIV-patient, the method comprising: assaying in a biological sample of the HIV patient one or more of: (i) a level of a microRNA (miRNA) that downregulated a peroxin; (ii) level a peroxisomal activity biomarker, and (iii) level of a substrate for a peroxisomal enzyme, wherein the HIV patient is receiving treatment with an agent that increases peroxisome activity; wherein the assaying provides guidance for providing or altering a level of the agent used for the treatment.

In certain cases, the HIV patient is receiving treatment with a peroxisome proliferator-activated receptor-α (PPARα) agonist. In certain cases, the PPARα agonist comprises a ligand of PPARα. In certain cases, the HIV patient is receiving treatment with chloro-N-(2-chloro-4-nitrophenyl)-2-hydroxybenzamide (CAS No. 50-65-7) (niclosamide) or salt, solvate, clathrate, hydrate, polymorph thereof.

In certain cases, the miRNA comprises miR-500a-5p, miR-34c-3p, miR-93-3p, or miR-381-3p and the method comprises comparing expression level of a microRNA (miRNA) selected from the group consisting of miR-500a-5p, miR-34c-3p, miR-93-3p, and miR-381-3p to a reference level of miR-500a-5p, miR-34c-3p, miR-93-3p, and miR-381-3p, respectively.

In certain cases, the reference is the expression level of a microRNA (miRNA) selected from the group consisting of miR-500a-5p, miR-34c-3p, miR-93-3p, and miR-381-3p in a normal subject. In other cases, the reference is the expression level of a microRNA (miRNA) selected from the group consisting of miR-500a-5p, miR-34c-3p, miR-93-3p, and miR-381-3p in the HIV patient prior to the start of treatment.

In certain embodiments, the method comprises comparing the peroxisomal activity biomarker to a reference. In certain cases, the reference is the level of the peroxisomal activity biomarker in a normal subject. In certain cases, the reference is the level of the peroxisomal activity biomarker in the HIV patient prior to the start of treatment.

In certain cases, the substrate for the peroxisomal enzyme being assayed in the methods disclosed herein comprises a long chain fatty acid comprising 14-21 carbon atoms and/or or a very long chain fatty acid comprising 22-26 carbon atoms.

BRIEF DESCRIPTION OF THE DRAWINGS

FIG. 10 shows that transfection of miRNA mimics that target PEX mRNAs leads to increased levels of innate immune mRNAs encoding IFIT2 (panel A) and IRF1 (panel B).

FIGS. 15A-15B show a list of potential target genes of differentially expressed miRNAs in brains of HAND compared to nonHAND patients by computational prediction.

FIG. 16 shows a list of oligonucleotide primers containing SEQ ID NOs: 1-23. Restriction endonuclease sites are bolded and underlined.

FIG. 17 shows that niclosamide potently and significantly inhibits HIV replication.

DETAILED DESCRIPTION

Figure 1:
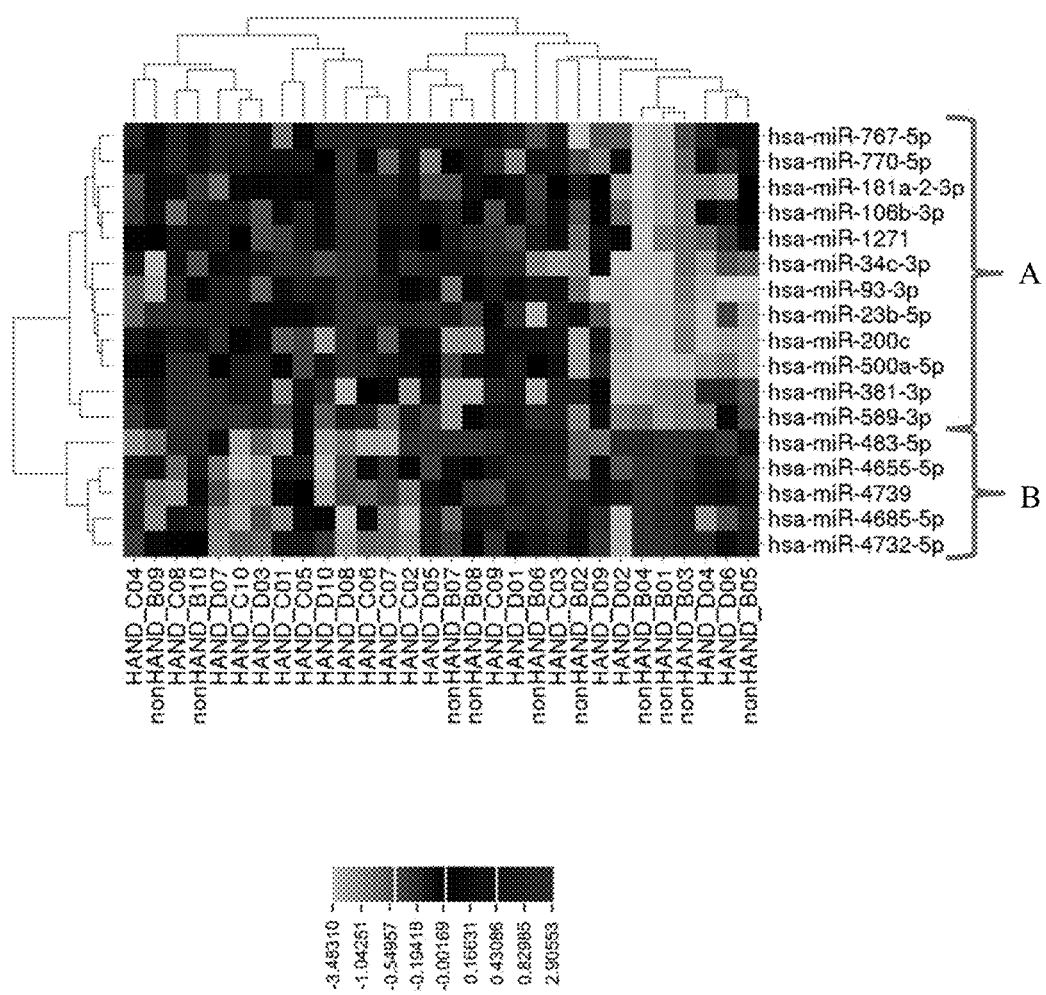
FIG. 1 shows distinct miRNA profile in brains of HAND patients.

The present disclosure provides methods of assessing likelihood of development of HIV-associated neurocognitive disorder (HAND) in a HIV patient. Also provided herein are methods for treating a HIV patient, such as, a HIV patient with increased level of a miRNA that downregulates a peroxin and/or decreased level of a peroxisomal activity biomarker and/or increased level of a substrate for a peroxisomal enzyme. The present disclosure also provides methods for monitoring efficacy of a treatment regimen for a HIV patient.

Before exemplary embodiments of the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials may now be described. Any and all publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a peroxisomal protein" includes a plurality of peroxisomal proteins and reference to "the reference" includes reference to one or more references, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent such publications may set out definitions of a term that conflicts with the explicit or implicit definition of the present disclosure, the definition of the present disclosure controls.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

The term "prognosis" as used herein refers to a prediction of likelihood of a particular outcome of a disease in a patient, such as likelihood of development of HAND in a HIV patient.

The terms "body fluid," "bodily fluid," and "biological fluid" are used interchangeably herein, refer to a biological sample of liquid from a subject, for example, a mammal, e.g., from a human. Such fluids include aqueous fluids such as blood (e.g., whole blood or a fraction thereof (e.g., serum, plasma), where the blood may be obtained from any arterial or venous source in the body), spinal fluid, and pericardial fluid. Particular bodily fluids that are of interest in the context of the present disclosure include whole blood, serum, plasma, and other blood-derived samples, wherein the term "blood sample" is meant to encompass whole blood or fractions thereof (e.g., serum, plasma). The types of sample can be selected so as to be compatible with the assay format.

The term "treating" or "treatment" of a condition or disease includes providing a clinical benefit to a subject, and includes: (1) inhibiting the disease, i.e., arresting or reducing the development of the disease or its symptoms, or (2) relieving the disease, i.e., causing regression of the disease or its clinical symptoms.

The terms "prevent", "preventing", "prevention" and the like refer to a course of action (such as administering an agent, e.g., a PPARα agonist or peroxisome activators) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state in a subject who has been diagnosed as having the condition. In certain embodiments, the methods of the present disclosure may be used to prevent progression of a HAND disorder, such as, progression from asymptomatic to a clinically diagnosed condition, and/or to prevent increase in severity of the disorder.

The phrase "therapeutically effective amount" refers to the administration of an agent to a subject, either alone or as a part of a pharmaceutical composition and either in a single dose or as part of a series of doses, in an amount that is capable of having any detectable, positive effect on any marker, symptom, aspect, or characteristics of a disease, disorder or condition when administered to a patient. The therapeutically effective amount can be ascertained by measuring relevant physiological effects, such as, increase in peroxisomal activity. The therapeutically effective amount can be adjusted in connection with the dosing regimen and diagnostic analysis of the subject's condition and the like.

The phrase "in a sufficient amount to effect a change" means that there is a detectable difference between a level of an indicator measured before (e.g., a baseline level) and after administration of a particular therapy. Indicators include any objective parameter (e.g., level of a blood marker) or subjective parameter (e.g., a subject's feeling of well-being or mental acuity).

The terms "individual," "subject," "host," and "patient," are used interchangeably herein and refer to any mammalian subject for whom prognosis, diagnosis, treatment, or therapy is desired, particularly humans. The mammalian subject may be a rodent, a feline, a canine, an equine, a bovine, a non-human primate, or a human. In certain embodiments, the "individual," "subject," "host," and "patient," may be a patient diagnosed as having HIV infection, and is referred to as "HIV patient".

As used herein, the terms "determining," "assessing," "assaying," "measuring," and "detecting" refer to both quantitative and semi-quantitative determinations and as such, the term "determining" is used interchangeably herein with "assaying," "measuring," and the like. Where a quantitative determination is intended, the phrase "determining an amount" of an analyte and the like is used. Where either a quantitative and semi-quantitative determination is intended, the phrase "determining a level" of an analyte or "detecting" an analyte is used.

"Quantitative" assays provide information on the amount of an analyte in a sample. Quantitative assay may provide information on the concentration of an analyte relative to a reference (control), and are usually reported numerically, where a "zero" value can be assigned where the analyte is below the limit of detection. "Semi-quantitative" assays involve presentation of a numeric representation of the amount of the analyte in the specimen that is relative to a reference (e.g., a threshold, e.g., normal threshold or an abnormal threshold), where a "zero" value can be assigned where the analyte is below the limit of detection. In general, semi-quantitative results are compared against an accompanying reference to provide a qualitative interpretation of the result.

"Normalized level" refers to level of a protein, RNA (e.g., miRNA or mRNA), enzymatic activity, substrate, or peroxisomes disclosed herein relative to level of a normalizing protein(s), RNA, enzymatic activity, normal number of peroxisomes or the like. In certain cases, where level of a protein or RNA is measured, the normalizing protein/RNA may such as a housekeeping protein/RNA. In certain cases, the measuring of a level of miRNA and/or peroxisomal activity biomarker may include determining a normalized level of the miRNA/biomarker. In other embodiments, the level may not be normalized.

As used herein, the term "level" in the context of a miRNA, a biomarker, a substrate disclosed herein refers to the amount of a RNA, protein, enzymatic activity, metabolite, or a substrate in a biological sample of a subject. The level may be an actual level (e.g., amount or concentration) or a relative level or a semi-quantitative level.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable excipient (e.g., pharmaceutically acceptable diluent, carrier or vehicle).

Formulations of the agents disclosed herein (e.g., an agent for increasing peroxisome activity) are generally dosed in vivo corresponding to the body weight of the subject. Due to the continuous breakdown of the active agent in the blood, the agent is normally administered at regular intervals. Those of skill in the art will readily appreciate that actual dosages and regimen will vary as a function of the agent, formulation, the severity of the symptoms, the susceptibility of the subject to treatment and/or side effects, and the like. Dosages are readily and routinely determinable by those of skill in the art by a variety of means.

Methods

The present disclosure provides methods for prognosis, treatment, and monitoring treatment of a HIV patient. Various steps and aspects of the methods will now be described in greater detail below.

In certain embodiments, a method for predicting likelihood of development of human immunodeficiency virus (HIV)-associated neurocognitive disorder (HAND) in a HIV patient is disclosed. The method may include assaying in a biological sample of the HIV patient an expression level of a miRNA that downregulates expression of a peroxin. As used herein, a peroxin may be any protein involved in biogenesis of peroxisomes and the downregulation of which protein may lead to decrease in peroxisome activity due a decrease in the number of peroxisomes and/or function of peroxisomes.

In certain aspects, a miRNA that downregulates expression of a peroxin may be a miRNA that downregulates expression of PEX2. In certain aspects, a miRNA that downregulates expression of a peroxin may be a miRNA that downregulates expression of PEX7. In certain aspects, a miRNA that downregulates expression of a peroxin may be a miRNA that downregulates expression of PEX11B. In certain aspects, a miRNA that downregulates expression of a peroxin may be a miRNA that downregulates expression of PEX7 and PEX11B. In certain aspects, a miRNA that downregulates expression of a peroxin may be a miRNA that downregulates expression of PEX13.

In certain aspects, the miRNA may be a miRNA that binds to a 3'UTR region of a peroxin protein encoding mRNA. In certain embodiments, the peroxin protein encoding mRNA may be PEX2, PEX7, PEX11B, or PEX13 encoding mRNA.

In certain embodiments, the miRNA may be selected from the group consisting of miR-500a-5p, miR-34c-3p, miR-93-3p, and miR-381-3p. In certain embodiments, the method for predicting likelihood of development of HAND may include assaying the expression level of at least two miRNAs in a biological sample of the HIV patient. For example, the method may include assaying for expression level of at least two of miR-500a-5p, miR-34c-3p, miR-93-3p, and miR-381-3p. In certain embodiments, the method for predicting likelihood of development of HAND may include assaying the expression level of at least three miRNAs in a biological sample of the HIV patient, e.g., at least three of miR-500a-5p, miR-34c-3p, miR-93-3p, and miR-381-3p. In certain embodiments, the method for predicting likelihood of development of HAND may include assaying the expression level of miR-500a-5p, miR-34c-3p, miR-93-3p, and miR-381-3p.

In certain aspects, the method for predicting likelihood of development of HAND in a HIV patient may further include comparing the expression level of a miRNA, determined by the assaying step, to a reference level. The reference level may be expression level of the miRNA in a reference subject. In certain embodiments, the reference subject may be a normal subject who does not have HIV or encephalitis. In certain embodiments, the reference subject may be a HIV patient who does not have HAND. In certain embodiments, the reference subject may be a HIV patient who does not have HAND or encephalitis. In certain embodiments, the reference subject may be a HIV patient who does not have HAND and encephalitis. The reference level may be a range of miRNA level determined from patients (e.g. HIV patients) who do not have HAND or encephalitis. An increased miRNA level in the HIV patient compared to a reference level is indicative of an increased risk of HAND in the HIV patient. For example, increased miRNA level in the HIV patient compared to the miRNA level in a subject who is HIV-positive and does not have HAND or encephalitis is indicative of an increased risk of HAND in the HIV patient.

In certain aspects, a significant increase in the miRNA expression level as compared to a reference level may indicate increased risk for HAND, for example, at least a 10% increase in the miRNA expression level as compared to a reference level may indicate increased risk for HAND. In certain aspects, at least a 20% increase, at least a 30% increase, at least a 40% increase, at least a 50% increase, at least a 60% increase, at least a 70% increase, at least a 80% increase, at least a 90% increase, at least a 100% increase, or more in the miRNA expression level as compared to a reference level may indicate increased risk for HAND.

In other aspects of the present disclosure, a method for predicting likelihood of development of HAND in a HIV patient may include assaying in a biological sample of the HIV patient a peroxisomal activity biomarker, where decreased level of the peroxisomal activity biomarker is indicative of increased risk for development of HAND in the HIV patient. Examples of peroxisomal activity biomarker include, peroxins which are proteins required for peroxisome biogenesis, peroxisome membrane proteins, peroxisomal enzymes, metabolites produced by peroxisomes, number of peroxisomes, and/or morphology of peroxisomes. Levels of a peroxin or a peroxisomal protein (e.g., a protein present in the membrane or matrix of peroxisomes) may be assayed by detecting the expression level of a mRNA encoding a peroxisomal activity biomarker and/or by detecting the expression level of a protein. Levels of a peroxisomal protein such as an enzyme may be measured by assaying activity of the enzyme, wherein a decreased enzymatic activity is indicative of an increased risk for development of HAND in a HIV patient. A peroxisomal activity biomarker may be a reaction product produced by action of a peroxisomal enzyme. Level of the reaction product may be measured, wherein a decreased level of the reaction product is indicative of an increased risk for development of HAND in a HIV patient. A peroxisomal activity biomarker may be a population of peroxisomes, where a decreased peroxisome population (i.e. lower number of peroxisomes) is indicative of a higher risk for developing HAND. A peroxisomal activity biomarker may be a normal morphology of peroxisomes, where a decrease in the number of peroxisomes with a normal morphology is indicative of a higher risk for developing HAND.

In certain cases, the method may include assaying expression level of one or more peroxins. The peroxin may be selected from the group consisting of PEX2, PEX19, PEX7, PEX11B and PEX13. In certain cases, the expression level of the peroxin or a mRNA encoding the peroxin may be detected. In certain cases, the method may include assaying expression level of at least two, at least three, at least four, or five of PEX2, PEX19, PEX7, PEX11B and PEX13.

In certain cases, the method may include assaying expression level of one or more peroxisomal enzymes. Assaying expression level of a peroxisomal enzyme may include assaying levels of a mRNA encoding the enzyme, assaying the levels of the enzyme, and/or assaying for catalytic activity of the enzyme. The peroxisomal enzyme may be dihydroxyactone-phosphate acyltransferase (DHAPAT), acyl-CoA oxidase (e.g., a flavin containing oxidase, such as Flavin adenine dinucleotide (FAD)-containing enzymes, for example, palmitoyl-CoA oxidase), D-amino acid oxidase, or glycolate oxidase.

In certain aspects, the biomarker being assayed may be a peroxisomal enzymatic activity reaction product, such as, 2-hexadecenoyl-CoA and/or one or more plasmalogens.

In certain aspects, the biomarker being assayed may be the number of peroxisomes in cells. In certain aspects, number of peroxisomes may be assessed by cytometry techniques, such as, laser scanning cytometry or by microscopy. In certain aspects, the biomarker being assayed may be morphology of peroxisomes which may be assayed by microscopy. These methods may also utilize specific binding members, such as, molecules that bind to components of peroxisomes may be include ligands or antibodies which may be detectably labeled.

In certain aspects, the method for predicting likelihood of development of HAND in a HIV patient may further include comparing the level of peroxisomal activity biomarker, determined by the assaying step, to a reference level. The reference level may be the level of peroxisomal activity biomarker in a reference subject. In certain embodiments, the reference subject may be a normal subject who does not have HIV or encephalitis. In certain embodiments, the reference subject may be a HIV patient who does not have HAND. In certain embodiments, the reference subject may be a HIV patient who does not have HAND or encephalitis. In certain embodiments, the reference subject may be a HIV patient who does not have HAND and encephalitis. The reference level may be a range of the level of peroxisomal activity biomarker determined from patients (e.g. HIV patients) who do not have HAND or encephalitis. A decreased level of peroxisomal activity biomarker in the HIV patient compared to a reference level is indicative of an increased risk of HAND in the HIV patient. For example, decreased level of peroxisomal activity biomarker in the HIV patient compared to the level of peroxisomal activity biomarker in a subject who is HIV-positive and does not have HAND or encephalitis is indicative of an increased risk of HAND in the HIV patient.

In certain aspects, a significant decrease in the level of peroxisomal activity biomarker as compared to a reference level may indicate increased risk for HAND, for example, at least a 10% decrease in the level of peroxisomal activity biomarker as compared to a reference level may indicate increased risk for HAND. In certain aspects, at least a 20% decrease, at least a 30% decrease, at least a 40% decrease, at least a 50% decrease, at least a 60% decrease, at least a 70% decrease, at least a 80% decrease, at least a 90% decrease, at least a 100% decrease, or more in the level of peroxisomal activity biomarker as compared to a reference level may indicate increased risk for HAND.

In certain embodiments, the method for determining likelihood of development of HAND in a patient may including assaying in a biological sample of the HIV patient a level of a substrate processed by enzymatic activity of peroxisomal enzymes, where an increase in level of the substrate is indicative of a higher likelihood that the HIV patient may develop HAND. Such substrates include long chain fatty acids and very long chain fatty acids, which may be saturated or unsaturated and may be conjugated to coenzyme A (CoA). In certain aspects, a significant increase in the substrate level as compared to a reference level may indicate increased risk for HAND, for example, at least a 10% increase in the substrate level as compared to a reference level may indicate increased risk for HAND. In certain aspects, at least a 20% increase, at least a 30% increase, at least a 40% increase, at least a 50% increase, at least a 60% increase, at least a 70% increase, at least a 80% increase, at least a 90% increase, at least a 100% increase, or more in the substrate level as compared to a reference level may indicate increased risk for HAND.

In certain embodiments, the method for determining likelihood of development of HAND in a patient may including assaying in a biological sample of the HIV patient one, two, or all three of: (i) an expression level of a microRNA (miRNA) that downregulates expression of a peroxin, wherein increased levels of the miRNA is indicative of increased risk for development of HAND in the HIV patient; (ii) a peroxisomal activity biomarker, wherein decreased level of the peroxisomal activity biomarker is indicative of increased risk for development of HAND in the HIV patient; and (iii) a level of a substrate of a peroxisomal enzyme, where increased levels of the miRNA is indicative of increased risk for development of HAND in the HIV patient.

In certain aspects, the method for predicting risk of HAND may further include reporting the results from the assaying and comparing steps. In other aspects, the method for predicting risk of HAND may further include recommending a treatment for the HIV patient. In some aspects, the method may include the assaying and comparing steps as disclosed herein and identifying the HIV patient as having a higher likelihood of developing HAND and further recommending treatments for reducing the likelihood of developing HAND.

In certain aspects, the method for predicting risk of HAND may further include treating a HIV patient identified as having an increased risk of HAND. In certain aspects, the treating of the HIV patient identified as having an increased risk of HAND may involve administering a therapeutically effective amount of an agent that increases peroxisomal activity.

According to certain embodiments, a method for treating a HIV patient identified as having increased risk of developing HAND may include administering at least one agent that increases peroxisomal activity. Also disclosed herein are methods for treating a HIV patient who has HAND.

In certain aspects, a method for treating a HIV patient identified as at risk for developing HAND or a HIV patient who has HAND may include administering an agonist for one or more of peroxisome proliferator-activated receptor-α (PPARα). According to certain embodiments, the agonist may be a PPARα ligand. Any PPARα agonist may be used for treatment of HIV patients identified as at risk for developing HAND or HAND patients (i.e., a HIV patient who had been diagnosed as having HAND). According to certain embodiments, the PPARα agonist may be a PPARα ligand, such as, a fibrate. In still other embodiments, the fibrate may include amphipathic carboxylic acids. Examples of fibrates useful for increasing peroxisome activity include fenofibrate, clofibrate, Wy-14643, the 2-arylthioacetic acid analogue of clofibrate, and bezafibrate. Ligands for PPARα include PPARα agonist oleylethanolamide. Additional compounds that may be used for treating HIV patients include dual PPARγ/α agonists such as KRP-297, DRF-2725 and AZ-242. In certain aspects, the method of treating a HIV patient at increased risk for developing HAND or a HIV patient having HAND may include administering a Thiazolidione (TZD) or an analog there for. According to certain embodiments, the method of treating a HIV patient at risk for developing HAND or a HAND patient may include administering fenofibrate. Fenofibrate is also known as 1-methylethyl 2-[4-(4-chlorobenzoyephenoxy]-2-methyl-propanoate. As used herein, fenofibrate refers to fenofibrate as well as derivatives and salts thereof.

In certain aspects, a method of treating a HIV patient identified as at risk for developing HAND may include administering at least one agent that increases peroxisomal activity thereby preventing or delaying the onset of HAND. The subject methods may delay onset of HAND by at least 1 month, 3 months, 6 months, 1 year, 3 years, 5 years, 10 years, 20 years, or more, e.g., 1 month-30 years, 3 months-20 years, 6 months-15 years, 1 year-15 years, or 1 year-10 years.

In certain aspects, a method of treating a HIV patient identified as at risk for developing HAND may include administering a peroxisome proliferator such as niclosamide or a salt, solvate, clathrate, hydrate, or polymorph thereof to the patient. The peroxisome proliferator may be administered in an amount effective to increase a peroxisome activity biomarker.

According to certain embodiments, a method for monitoring treatment of a HIV patient is also disclosed. In certain embodiments, the HIV patient may be a patient identified as having increased level of a miRNA that downregulates a peroxin and/or decreased level of a peroxisomal activity biomarker and/or increased level of a substrate of a peroxisomal enzyme. In certain embodiments, the HIV patient may be a patient diagnosed as having HAND. In certain embodiments, the HIV patient may be receiving a treatment for HIV, such as, an anti-retroviral therapy (ART) or a treatment for preventing development of HAND, such as a method disclosed herein. In certain embodiments, the method for monitoring treatment may include assaying a biological sample of the HIV patient receiving treatment for level of an expression level of a microRNA (miRNA) that downregulates expression of a peroxin and/or level of a peroxisomal activity biomarker. The miRNA and/or peroxisomal activity biomarker and/or peroxisome substrate assayed may be the miRNA and/or peroxisomal activity biomarker and/or the peroxisome substrate provided herein.

In certain embodiments, the method for monitoring treatment may include comparing the level of a microRNA (miRNA) that downregulates expression of a peroxin and/or level of a peroxisomal activity biomarker and/or peroxisome substrate to an appropriate reference. In certain embodiments, the reference may be the level of the miRNA and/or peroxisomal activity biomarker and/or peroxisome substrate, respectively, in a biological sample of the HIV patient prior to the start of treatment. In certain embodiments, the reference may be the level of the miRNA and/or peroxisomal activity biomarker and/or peroxisome substrate in a normal subject who does not have HIV infection. A positive change in the level, i.e., a change indicative of improvement in peroxisome activity is indicative of effectiveness of treatment. A lack of change in level or a negative change of level may be indicative of lack of effectiveness of treatment and a change in treatment regimen may be recommended.

In other embodiments, the method for monitoring treatment may include (i) assaying a biological sample of a HIV patient for level of an expression level of a microRNA (miRNA) that downregulates expression of a peroxin and/or level of a peroxisomal activity biomarker; (ii) administering an agent that increases peroxisome activity; assaying a biological sample of a HIV patient for level of an expression level of the miRNA and/or level of a peroxisomal activity biomarker; (iii) comparing the level to the level of the corresponding miRNA and/or peroxisomal activity biomarker measured in step (i), wherein a lack of change in the level of the measured miRNA and/or peroxisomal activity biomarker indicates that the treatment is ineffective. In certain aspects, the method may further include administering a higher dosage of the agent that increases peroxisome activity.

In other embodiments, the method for monitoring treatment may include (i) assaying a biological sample of a HIV patient for level of level of a peroxisomal activity biomarker; (ii) administering an agent that increases peroxisome activity; (iii) assaying a biological sample of a HIV patient for level of the peroxisomal activity biomarker; (iv) comparing the level obtained in step (iii) to the level of the peroxisomal activity biomarker measured in step (i), wherein a lack of change in the level of the peroxisomal activity biomarker indicates that the treatment is ineffective. In certain aspects, the method may further include administering a higher dosage of the agent that increases peroxisome activity.

In other embodiments, the method for monitoring treatment may include (i) assaying a biological sample of a HIV patient for level of level of a peroxisomal activity biomarker; (ii) administering an agent that increases peroxisome activity; (iii) assaying a biological sample of a HIV patient for level of the peroxisomal activity biomarker; (iv) comparing the level obtained in step (iii) to the level of the peroxisomal activity biomarker measured in step (i), wherein an increase in the level of the peroxisomal activity biomarker measured in step (iii) indicates that the treatment is effective. In certain aspects, the method may further include terminating the treatment or administering a lower dosage of the agent that increases peroxisome activity.

In other embodiments, the method for monitoring treatment may include (i) administering an agent that increases peroxisome activity; (ii) assaying a biological sample of a HIV patient for level of a peroxisomal activity biomarker; (iii) comparing the level obtained in step (ii) to a reference level indicative of normal level of the peroxisomal activity biomarker (e.g., level in a subject who does not have HIV), wherein when the level of the peroxisomal activity biomarker measured in step (ii) is comparable to the normal level, the treatment is effective. In certain aspects, the method may further include terminating the treatment or administering a lower dosage of the agent that increases peroxisome activity.

In other embodiments, the method for monitoring treatment may include (i) administering an agent that increases peroxisome activity; (ii) assaying a biological sample of a HIV patient for level of a peroxisomal activity biomarker; (iii) comparing the level obtained in step (ii) to a reference level indicative of normal level of the peroxisomal activity biomarker (e.g., level in a subject who does not have HIV), wherein when the level of the peroxisomal activity biomarker measured in step (ii) is lower than the normal level, the treatment is ineffective. In certain aspects, the method may further include administering a higher dosage of the agent that increases peroxisome activity.

In other embodiments, the method for monitoring treatment may include (i) assaying a biological sample of a HIV patient for level of a peroxisomal substrate (i.e., a substrate for a peroxisomal enzyme); (ii) administering an agent that increases peroxisome activity; (iii) assaying a biological sample of a HIV patient for level of the peroxisomal substrate; (iv) comparing the level obtained by step (iii) to the level of the peroxisomal substrate measured in step (i), wherein a lack of change in the level of the peroxisomal substrate indicates that the treatment is ineffective. In certain aspects, the method may further include administering a higher dosage of the agent that increases peroxisome activity.

In other embodiments, the method for monitoring treatment may include (i) assaying a biological sample of a HIV patient for level of a peroxisomal substrate (i.e., a substrate for a peroxisomal enzyme); (ii) administering an agent that increases peroxisome activity; (iii) assaying a biological sample of a HIV patient for level of the peroxisomal substrate; (iv) comparing the level obtained by step (iii) to the level of the peroxisomal substrate measured in step (i), wherein an increase in the level of the peroxisomal substrate indicates that the treatment is ineffective. In certain aspects, the method may further include administering a higher dosage of the agent that increases peroxisome activity.

In other embodiments, the method for monitoring treatment may include (i) assaying a biological sample of a HIV patient for level of a peroxisomal substrate (i.e., a substrate for a peroxisomal enzyme); (ii) administering an agent that increases peroxisome activity; (iii) assaying a biological sample of a HIV patient for level of the peroxisomal substrate; (iv) comparing the level obtained by step (iii) to the level of the peroxisomal substrate measured in step (i), wherein a decrease in the level of the peroxisomal substrate measured in step (iii) indicates that the treatment is effective. In certain aspects, the method may further include administering a lower dosage of the agent that increases peroxisome activity or terminating the treatment.

In certain cases a method includes administering agent that increases peroxisome activity to an individual having HAND; obtaining a biological sample from the individual; assessing a level of one or more of (i) a miRNA that downregulates expression of a peroxin, (ii) a peroxisome activity biomarker, (iii) a substrate of a peroxisomal enzyme, in the biological sample obtained from the individual; comparing the level to level of (i), (ii), and/or (iii), respectively, present before the administering, wherein a decrease in the level of (i), an increase in the level of (ii), and/or a decrease in the level of (iii), after the administering provides an indication that the administering has a positive clinical effect on the individual; and if a positive clinical effect is not observed, adjusting dosage of the gent that increases peroxisome activity till positive clinical effect is observed.

Methods for Assaying Biological Sample

Micro RNA Measurement

The assaying of a miRNA disclosed herein may be performed using any suitable technique. In some cases, detection of the one or more microRNAs can be accomplished by altering the tissue or body fluid sample so that the microRNAs produce a signal. In some forms, the alteration of the tissue or body fluid sample comprising amplifying the microRNAs. For example, the microRNAs can be amplified via polymerase chain reaction (PCR), such as, quantitative or real time PCR. In some forms, the alteration can be hybridization of a probe to the microRNAs or amplified copies of the microRNA sequences. In some embodiments, miRNA may be assayed by hybridizing miRNA present in a biological sample to a microarray, such as, a microarray chip that includes oligonucleotides that hybridize to a target miRNA.

In certain embodiments, a microarray chip comprising oligonucleotides complementary to one or more miRNAs disclosed herein may be used in the methods of the present disclosure. In certain aspects, a method for assaying a level of a miRNA may include contacting a biological sample from a HIV patient with a microarray chip comprising oligonucleotides complementary to one, two, three, or four of miR-500a-5p, miR-34c-3p, miR-93-3p, and miR-381-3p.

As noted herein, an increase in level of one or more of the miRNAs that downregulate a peroxin (i.e., proteins required for peroxisome formation) is indicative of an increased likelihood of a HIV patient developing HAND and may indicate that the patient would benefit from a treatment with an agent for increasing peroxisome activity.

Peroxisomal Activity Biomarker Measurement

As noted herein a peroxisomal activity biomarker may be a peroxin, a protein present in peroxisomes, e.g., a peroxisomal membrane protein, a peroxisomal matrix protein, peroxisome quantity, and/or peroxisome morphology.

Level of a peroxin or a peroxisomal protein (e.g., protein present in peroxisome membrane or matrix, e.g., enzymes) may be measured by any suitable technique for measuring protein or mRNA level. For example, mRNA level may be measured by using probes that hybridize to the mRNA and/or by amplification of the mRNA (e.g., by PCR or RT-PCR). Suitable methods of detecting a protein, such as, a peroxin or a peroxisomal protein include but are not limited to binding assays, e.g., immunoassays, direct detection assays, and proteomic detection assays. Methods for protein/RNA detection may vary and may be either qualitative or quantitative Immunoassays may include ELISA, immunoblot assays, flow cytometric assays, immunohistochemical assays, radioimmuno assays, immunoblot assays, immunofluorescent assays, chemiluminescent assays, radioimmunoassays assay and other polypeptide detection strategies. Proteins of interest may also be measured using mass spectrometry. For example, a sample may be analyzed by generating gas phase ions from the sample, which are then separated according to their mass-to-charge ratio (m/z) and detected. Methods of generating gas phase ions from a sample include electrospray ionization (ESI), matrix-assisted laser desorption-ionization (MALDI), surface-enhanced laser desorption-ionization (SELDI), chemical ionization, and electron-impact ionization (EI). Separation of ions according to their m/z ratio can be accomplished with any type of mass analyzer, including quadrupole mass analyzers (Q), time-of-flight (TOF) mass analyzers, magnetic sector mass analyzers, 3D and linear ion traps (IT), Fourier-transform ion cyclotron resonance (FT-ICR) analyzers, and combinations thereof (for example, a quadrupole-time-of-flight analyzer, or Q-TOF analyzer).

Detection, analysis, and/or quantification of proteins of interest (e.g., peroxins or peroxisomal proteins) as performed by the detection methods, as described herein, may further include an evaluation of the results of the assay by comparison to a control or reference standard. For example, in some instances, the results of a particular immunoassay or direct detection assay are compared to a reference standard, e.g., a control or a standard. Any suitable control or standard for a particular immunoassay, or direct detection assay may be employed including control assays performed concurrently with or immediately before or after the detection assay (e.g., internal or external control assays or reactions). Such control assays will vary but may include providing with the assay a known concentration or known amount of one or more of the analytes to be detected or measured, e.g., a positive control. In some instances, a control assay may include a number of different known concentrations of a particular analyte such that qualitative assessments of the amount of the analyte present in the sample may be made by comparison to the control assay results with the various known concentrations. In some instances, control assays for a particular immunoassay or direct detection assay need not necessarily require performing a control assay or control reaction and may instead make use of the results of previously performed control reactions. In some instances, such results may be provided as reference results or reference standards, e.g., as a single values (i.e. a threshold), as a range of values, as multiple values provided in a table, in a chart, in a graph, as an image or illustration or diagram of an assay result, e.g., a picture of a positive result or negative result or pictures of particular quantitative or qualitative results.

In certain cases, a normalizing protein, for example, a housekeeping protein such as action (e.g., β-actin) may also be detected simultaneously or in parallel and used to normalize the biomarker protein levels.

A peroxisomal biomarker may be a peroxisomal enzyme which may be measured by assaying level of mRNA encoding the enzyme, level of the enzyme, and/or activity of the enzyme. In certain embodiments, enzymatic activity may be measured by assaying for the presence of a reaction product produced by action of the enzyme on a substrate. As noted herein, a decrease in level of a peroxisomal enzyme, a decrease in activity of a peroxisomal enzyme, and/or a decrease in level of a product by activity of a peroxisomal enzyme is indicative of an increased likelihood of developing HAND. In certain embodiments, the peroxisomal enzyme is not catalase. In certain embodiments, the peroxisomal enzyme is peroxisomal acyl-CoA oxidase (e.g., a flavin containing oxidase, such as Flavin adenine dinucleotide (FAD)-containing enzymes, for example, palmitoyl-CoA oxidase), D-amino acid oxidase, or DHAPAT.

Measurement of Substrate for a Peroxisomal Enzyme

In certain embodiments, the methods for predicting likelihood of development of HAND in a HIV patient may include assaying a biological sample obtained from the patient for a level of a substrate processed by a peroxisomal enzyme. In certain embodiments, the substrate may be a long chain fatty acid (LFA) or a very long chain fatty acid (VLFA). The LFA and VLFA may be saturated or unsaturated fatty acid (e.g., polyunsaturated fatty acids). The detection and/or measurement of the LFA and VLFA may be performed using any reliable technique, such as, mass spectrometry, chromatography, e.g., gas chromatography. In certain embodiments, the substrate may be detected in a liquid biological sample from the HIV patient, e.g., from a blood sample (such as, a serum or plasma sample) or a CSF sample.

Biological Samples

A biological sample can be any sample in which miRNAs or peroxisomal proteins may be present. As noted above, biological samples of liquid from a mammal, e.g., from a human may be assayed to detect miRNAs or peroxisomal proteins levels. Such fluids include aqueous fluids such as blood (e.g., whole blood or a fraction thereof (e.g., serum, plasma)), cerebrospinal fluid, and the like. In certain embodiments, the biological sample may be cells obtained from a body fluid sample, such as, cells obtained from a whole blood sample or from CSF. Examples of cells that can be assayed include, platelets, red blood cells, white blood cells, monocytes, etc.

In certain embodiments, the biological sample may be a body tissue sample such as a biopsy sample. The biopsy sample may be obtained from brain or spinal cord of a subject.

A sample volume can be any volume that is compatible with the specific assay format. In some embodiments, the sample will be diluted in a suitable solution prior to assaying for the levels of miRNA or peroxisomal proteins. In general, a solution suitable for diluting a biological sample will include a buffer, such as phosphate buffered saline (PBS), and may include additional reagents, such as for example, a non-specific blocking agent, such as bovine serum albumin (BSA), a detergent, such as TRITON-X-100, TWEEN-20 and the like.

Appropriate control samples for the assay include biological samples, such as body fluid sample, e.g., blood sample collected from subjects who are diagnosed has not having HIV/AIDS, or samples which contain a known, predetermined amount of the assay target (i.e., a positive control). An example of a positive control may be sample containing the target "analyte" being detected, such as, miRNA(s) being measured, the target peroxisomal protein (s) being measured, a peroxisomal enzyme whose activity is being assessed, a substrate for a peroxisomal enzyme. In these cases, the control samples provide an assurance that the assay has been performed correctly and the reagents are stable when the expected results are obtained from the controls.

In certain embodiments, the biological sample may be a blood sample. The blood sample may be collected by a standard technique and stored using standard protocols prior to assaying. In certain cases, the blood sample may include anti-coagulation factors.

The biological sample may be processed prior to the assaying. In certain cases, the biological sample may be diluted or stabilized, and the like. The sample may be treated in a variety of ways so as to enhance detection of the level of miRNA or peroxisomal proteins. For example, where the sample is blood, the red blood cells may be removed from the sample (e.g., by centrifugation) prior to assaying. Detection of levels of miRNA or peroxisomal proteins may also be enhanced by concentrating the sample using procedures well known in the art (e.g. acid precipitation, alcohol precipitation, salt precipitation, hydrophobic precipitation, filtration (using a filter which is capable of retaining molecules greater than 30 kD, e.g. Centricon 30™), affinity purification). In certain cases, certain types of proteins may be depleted from the sample before the assay is performed.

Subjects

Subjects amenable to methods described herein are mammalian subjects, for example feline, canine, bovine, equine, or human subjects. The terms "subject" and "patient" are used interchangeably.

The subjects amenable to methods described herein include HIV/AIDS patients. The terms "HIV/AIDS patient" and "HIV patient" are used interchangeably to refer to subjects having HIV infection. A subject who may be given a prognosis, diagnosis, treatment, and/or monitored using the methods of the present disclosure may be a subject who has been diagnosed as having HIV infection. In certain cases, the HIV patient may have no discernible symptoms associated with HIV/AIDS other than being positive for HIV. In certain embodiments, the HIV patient may have been diagnosed as having asymptomatic HIV infection or chronic HIV infection during which the patient may not display symptoms of AIDS. In certain embodiments, the HIV patient may have at least one or more symptoms associated with AIDS. In some embodiments, the HIV patient may have advanced HIV disease including CD4 count of <100 cells/μL, wasting, high viral load (e.g., high plasma HIV RNA).

In certain embodiments, the methods of the present disclosure may be carried out on a biological sample obtained from a HIV patient who is receiving anti-retroviral therapy (ART). In some embodiments, the methods of the present disclosure may be carried out on a biological sample obtained from a HIV patient who is not receiving ART.

In certain embodiments, the methods of the present disclosure may be carried out on a biological sample obtained from a HIV patient who is not receiving a PPARα agonist, such as, fenofibrate.

In certain embodiments, the methods of the present disclosure may be carried out on a biological sample obtained from a HIV patient who is receiving a PPARα agonist, such as, fenofibrate.

In certain embodiments, the HIV patient may have normal triglyceride and/or normal cholesterol levels. In certain embodiments, the treatment methods disclosed herein may include administering a PPARα agonist, such as, fenofibrate to a HIV patient who does not have hyperlipidemia or hypercholesterolemia or both.

In some embodiments, the HIV patient may not have HIV-associated neurocognitive disorders (HAND). As used herein, the term HAND encompasses asymptomatic neurocognitive impairment (ANI), mild neurocognitive disorder (MND), and HIV-associated dementia (HAD). The prognostic methods disclosed herein may be used to predict the likelihood of such a patient developing HAND. A patient identified as having an increased likelihood of developing HAND may be treated using the methods disclosed herein. In addition, a patient identified as having an increased likelihood of developing HAND may be monitored using the methods disclosed herein. The monitoring may be performed in conjunction with a treatment to prevent or delay development of HAND or without a treatment to prevent or delay development of HAND. The monitoring may be performed in conjunction with a treatment to reduce HIV replication, such as ART. In other embodiments, the monitoring may be performed on a patient who is not receiving a treatment to reduce HIV replication, such as ART.

In some embodiments, the HIV patient may have a HIV-associated neurocognitive disorder (HAND). In certain embodiments, a patient may be identified as a HIV patient by conducting a test for HIV. A diagnosis of HAND may be performed on the HIV patient by conducting neurocognitive testing and/or by assessing functional impairment. A HIV patient may have a particular category of HAND. In some embodiments, the HIV patient may have asymptomatic neurocognitive impairment (ANI) which is determined by neurocognitive testing and is not apparent clinically. In some embodiments, the HIV patient may have mild neurocognitive disorder (MND) which is a diagnosis of exclusion; it may be made clinically if neurocognitive testing is not available, and it involves mild functional impairment. In some embodiments, the HIV patient may have HIV-associated dementia (HAD) which involves moderate to severe functional impairment. As used herein, development of HAND encompasses development of ANI, MND, or HAD.

In some embodiments, the HIV patient may have a HIV-associated neurocognitive disorder (HAND). Such a HIV-HAND patient may be treated using the method disclosed herein. For example, the HIV-HAND patient may be treated by administration of a PPARα agonist. In addition, the HIV-HAND patient may be monitored using the methods disclosed herein to determine whether the HAND is progressing or is improving. The monitoring may be performed using the methods disclosed herein.

Treatment

A HIV patient may be administered one or more agents that increase peroxisome activity. As used herein, the term "peroxisome activity" refers to a function of peroxisomes which may be measured by assaying a peroxisome biomarker, such as a peroxisomal protein or a metabolite produced by activity of peroxisomes. Peroxisome function may also be measured by assessing number of peroxisomes, peroxisome morphology, and the like. Peroxisome function may also be assayed by determining whether a substrate for a peroxisomal enzyme is accumulating. An accumulation of a substrate that is processed by peroxisomes may be reflected by an increase in level of the substrate in the body.

In certain embodiments, an agent that increases peroxisome activity may be an agent that decreases activity of miRNAs that decrease peroxisome formation. In certain embodiments, an agent that increases peroxisome activity may be siRNA that targets one or more miRNAs that decrease peroxisome formation. In certain aspects, a chemically modified anti-miR oligonucleotides designed to sterically inhibit microRNA via complementary base pairing may be used to sequester the miRNA and inhibit it from binding a mRNA encoding a peroxin. In certain embodiments, an agent that increases peroxisome activity may be an antibody that binds and inhibit activity of miRNAs that decrease peroxisome formation.

In certain embodiments, an agent that increases peroxisome activity may be an agent that increases levels of proteins required for biogenesis of peroxisomes. Examples of such peroxisome biogenesis proteins include peroxins (PEX) such as, PEX1, PEX2 (also known as peroxisomal membrane protein 3-PXMP3), PEX3, PEX5, PEX6, PEX7, PEX10, PEX11A, PEX11B, PEX11G, PEX12, PEX13, PEX14, PEX16, PEX19, and PEX26.

In certain embodiments, an agent that increases peroxisome activity may be an agent that increases levels of proteins required for formation of peroxisomal membrane.

In certain embodiments, an agent that increases peroxisome activity may be an agent that increases import of proteins into peroxisomal matrix. In certain embodiments, the agent may increase activity of a PEX such as, PEX2, PEX7, and/or PEX13.

In certain embodiments, an agent that increases peroxisome activity may be an agent that increases peroxisome proliferation. In certain embodiments, the agent may increase activity of a PEX such as, PEX11B. In certain embodiments, treatment of HIV in a subject may include administering to the subject an agent that increases peroxisome proliferation. In certain cases, an agent that increases peroxisome proliferation may be a peroxisome proliferator such as, 5-chloro-N-(2-chloro-4-nitrophenyl)-2-hydroxybenzamide (CAS No. 50-65-7), or a pharmaceutically acceptable salt, solvate, clathrate, hydrate or polymorph thereof or 4-phenylbutyrate (PBA) or a pharmaceutically acceptable salt, solvate, clathrate, hydrate or polymorph thereof.

In certain cases, an agent that increases peroxisome proliferation may be a peroxisome proliferator such as, 5-chloro-N-(2-chloro-4-nitrophenyl)-2-hydroxybenzamide which is also known as niclosamide. The preparation of this compound is described in U.S. Pat. No. 3,079,297. Treatment of a subject with HIV with a peroxisome proliferator such as niclosamide may result in decreased replication of HIV in the subject as compared to replication prior to the treatment. In certain cases, administering a peroxisome proliferator such as niclosamide to a subject with HIV may result in decreased replication of HIV in the subject as compared to replication prior to the administering and may also result in increased expression of peroxisomal proteins such as, PEX7.

Pharmaceutically acceptable salt, solvate, clathrate, hydrate or polymorph of niclosamide are described in WO2017191420A1 which is herein incorporated by reference. In certain cases, 5-chloro-N-(2-chloro-4-nitrophenyl)-2-hydroxybenzamide may be in the form of salts including inorganic or organic base. Inorganic bases may be sodium, potassium, magnesium or calcium. Organic bases may be amines, amino alcohols, basic amino acids such as lysine or arginine, or compounds carrying a quaternary ammonium functional group, such as, for example betaine or choline. In certain embodiments, 5-chloro-N-(2-chloro-4-nitrophenyl)-2-hydroxybenzamide may be in the form of a salt with ethanolamine. The preparation of this salt is described for example in U.S. Pat. No. 3,113,067. The term "polymorph" refers to any form or mixture of amorphous or crystalline forms of 5-chloro-N-(2-chloro-4-nitrophenyl)-2-hydroxybenzamide.

In certain embodiments, an agent that increases peroxisome function may a PPARα agonist. In certain embodiments, the PPARα agonist may be fenofibrate or a salt or derivative thereof.

In certain embodiments, the treatment methods contemplated herein may increase peroxisomal activity, such as, level of peroxisomal proteins, metabolites produced by peroxisomes, and/or number of peroxisomes by at least 5% (e.g., at least 10%, 20%, 30%, 50%, 60%, 70%, 80%, or 90%) compared to that in the absence of administration of an agent for increasing peroxisomal activity.

In certain embodiments, the treatment methods contemplated herein may increase peroxisomal activity and thereby decrease level of a substrate, processed by a peroxisomal enzyme, by at least 5% (e.g., at least 10%, 20%, 30%, 50%, 60%, 70%, 80%, or 90%) compared to that in the absence of administration of an agent for increasing peroxisomal activity.

Formulations

In particular embodiments of the present disclosure, one or more of the aforementioned agents, such as, an agent for increasing peroxisome activity, is formulated to yield a pharmaceutical composition or formulation, wherein the composition also includes one or more pharmaceutically acceptable diluents, carriers or excipients. In certain embodiments, a pharmaceutical composition also includes at least one additional prophylactic or therapeutic agent.

Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that could be used in the pharmaceutical compositions and dosage forms. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EPIPEN®)), whereas a multi-use container (e.g., a multi-use vial) is provided in other embodiments. Any drug delivery apparatus may be used to deliver the agents, including implants (e.g., implantable pumps) and catheter systems, both of which are well known to the skilled artisan. Depot injections, which are generally administered subcutaneously or intramuscularly, may also be utilized to release the agents disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed including synthetic mono- or diglycerides. Moreover, fatty acids such as oleic acid find use in the preparation of injectables. Prolonged absorption of particular injectable formulations can be achieved by including an agent that delays absorption (e.g., aluminum monostearate or gelatin).

The pharmaceutical compositions containing the active ingredient (e.g., agents for increasing peroxisomal activity of the present disclosure) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The agents contemplated by the present disclosure may be in the form of any other suitable pharmaceutical composition (e.g., sprays for nasal or inhalation use) currently known or developed in the future.

The concentration of an agent in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of the disclosed agents, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation.

Depot injections, which are generally administered subcutaneously or intramuscularly, may also be utilized to release the agents disclosed herein over a defined period of time. Depot injections are usually either solid- or oil-based and generally comprise at least one of the formulation components set forth herein. One of ordinary skill in the art is familiar with possible formulations and uses of depot injections.

Regarding antibodies, in an exemplary embodiment an antibody or antibody fragment of the present disclosure is stored at 10 mg/ml in sterile isotonic aqueous saline solution for injection at 4° C. and is diluted in either 100 ml or 200 ml 0.9% sodium chloride for injection prior to administration to the subject. The antibody is administered by intravenous infusion over the course of 1 hour at a dose of between 0.2 and 10 mg/kg. In other embodiments, the antibody is administered by intravenous infusion over a period of between 15 minutes and 2 hours. In still other embodiments, the administration procedure is via subcutaneous bolus injection.

The present disclosure contemplates methods wherein an agent of the present disclosure is administered to a subject at least twice daily, at least once daily, at least once every 48 hours, at least once every 72 hours, at least once weekly, at least once every 2 weeks, or once monthly.

Combination Therapy

The present disclosure contemplates the use of an agent provided herein in combination with one or more active therapeutic agents or other prophylactic or therapeutic modalities. In such combination therapy, the various active agents frequently have different mechanisms of action. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, an agent for increasing peroxisome activity is administered or applied sequentially, e.g., where one agent is administered prior to one or more other agents. In other embodiments, two or more agents are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure. In certain examples, two different agents for increasing peroxisome activity may be administered simultaneously or sequentially (in any order).

The agents of the present disclosure can be used in combination with other agents useful in the treatment, prevention, suppression or amelioration of the diseases, disorders or conditions set forth herein.

The present disclosure contemplates combination therapy with numerous agents (and classes thereof), including 1) PPAR alpha agonists such as fenofibric acid derivatives (e.g., gemfibrozil, clofibrate, ciprofibrate, fenofibrate, bezafibrate); 2) one or more anti-miR oligonucleotides that bind to a target miRNA, such as, miR-500a-5p, miR-34c-3p, miR-93-3p, and miR-381-3p; or 3) one or more antibodies that inhibit activity of one of more of miR-500a-5p, miR-34c-3p, miR-93-3p, and miR-381-3p, combined with one or more 1) PPAR gamma agonists; 2) dual-acting PPAR agonists (e.g., ZYH2, ZYH1, GFT505, chiglitazar, muraglitazar, aleglitazar, sodelglitazar, and naveglitazar), pan-acting PPAR agonists; 3) peroxisome proliferators such as niclosamide; and 3) anti-retroviral drugs, such as, (i) nucleoside reverse transcriptase inhibitors (e.g., Zidovudine (Retrovir, AZT), Tenofovir, a nucleotide analog (Viread, TDF), Truvada (combination of emtricitabine and tenofovir); (ii) Non-nucleoside reverse transcriptase inhibitors (e.g., Nevirapine (Viramune, NVP), Delavirdine (Rescriptor, DLV), Efavirenz (Sustiva or Stocrin, EFV, also part of Atripla), Etravirine (Intelence, ETR), Rilpivirine (Edurant, RPV, also part of Complera or Epivlera), (iii) Protease inhibitors (e.g., Saquinavir (Invirase, SQV), Indinavir (Crixivan, IDV), Ritonavir (Norvir, RTV), Nelfinavir (Viracept, NFV), Amprenavir (Agenerase, APV), Lopinavir/ritonavir (Kaletra or Aluvia, LPV/RTV), Atazanavir (Reyataz, ATZ), Fosamprenavir (Lexiva, Telzir, FPV), Tipranavir (Aptivus, TPV), Darunavir (Prezista, DRV); (iv) Entry inhibitors (e.g. Enfuvirtide (Fuzeon, ENF, T-20), Maraviroc (Selzentry or Celsentri, MVC); or (v) HIV integrase inhibitors, e.g., Raltegravir (Isentress, RAL), Elvitegravir (EVG, part of the combination Stribild), or Dolutegravir (Tivicay, DTG).

In one embodiment, treatment with at least one agent for increasing peroxisome activity and at least one agent for reducing HIV load is maintained over a period of time. In another embodiment, treatment with the at least one agent for reducing HIV load is reduced or discontinued (e.g., when the subject is stable), while treatment with an agent for increasing peroxisome activity is maintained at a constant dosing regimen. In a further embodiment, treatment with the at least one agent for reducing HIV load is reduced or discontinued (e.g., when the subject is stable), while treatment with an agent for increasing peroxisome activity is reduced (e.g., lower dose, less frequent dosing or shorter treatment regimen). In yet another embodiment, treatment with the at least one agent for reducing HIV load is reduced or discontinued (e.g., when the subject is stable), and treatment with an agent for increasing peroxisome activity is increased (e.g., higher dose, more frequent dosing or longer treatment regimen). In yet another embodiment, treatment with at least one agent for reducing HIV load is maintained and treatment with an agent for increasing peroxisome activity is reduced or discontinued (e.g., lower dose, less frequent dosing or shorter treatment regimen). In yet another embodiment, treatment with one agent for reducing HIV load and treatment with an agent for increasing peroxisome activity are reduced or discontinued (e.g., lower dose, less frequent dosing or shorter treatment regimen).

Utility

The methods of the present disclosure find use in a variety of different clinical applications, including assessing likelihood of a HIV patient developing HAND. The assessment of likelihood of a HIV patient developing HAND may be used for guiding treatment of the patient which may prevent or at least delay onset of HAND.

The methods of the present disclosure also find use in treating a HIV patient with an agent for increasing peroxisome activity, which patient may benefit from this treatment. Since a treatment with an agent for increasing peroxisome activity may have side effects, it is desirable to identify a HIV patient who may benefit from this treatment. Such a HIV patient may have increased levels of one or more miRNAs disclosed herein and/or decreased level of a peroxisomal activity biomarker and/or increased level of a substrate for a peroxisomal enzyme compared to a control or reference level. The control or reference level may be obtained from a normal subject or a HIV patient who does not have HAND or encephalitis or both.

Thus, in certain embodiments, the presently disclosed methods include a method for assaying in a biological sample of a HIV patient: (i) an expression level of a microRNA (miRNA) that downregulates expression of a peroxin, or (ii) level of a peroxisomal activity biomarker; or (iii) a substrate for peroxisomal enzyme. The biological sample may be a body fluid sample, such as, a blood sample, a serum sample, a plasma sample, or a cerebrospinal fluid sample. In certain cases, the miRNA may be miR-500a-5p, miR-34c-3p, miR-93-3p, and/or miR-381-3p. In certain cases, the peroxisomal activity biomarker may be PEX2, PEX19, PEX7, PEX11B, and/or PEX13. In certain cases, the peroxisomal activity biomarker may be a peroxisomal enzyme such as dihydroxyactone-phosphate acyltransferase (DHAPAT) or glutaryl-CoA oxidase.

In certain cases, if the HIV patient has increased levels of the miRNA, decreased level of the peroxisomal activity biomarker, and/or increased levels of a substrate for a peroxisomal enzyme, the method may further include treating the HIV patient with an agent that increases peroxisome activity. The agent may be one or more of the agents provided herein.

The methods of the present disclosure also find use in monitory effectiveness of treatment regimen of a HIV patient. The miRNAs and peroxisomal activity biomarkers provided herein may be assayed for assessing effectiveness of a treatment regimen and for guiding modifications to the treatment regimen.

EXAMPLES

As can be appreciated from the disclosure provided above, the present disclosure has a wide variety of applications. Accordingly, the following examples are put forth so as to provide those of ordinary skill in the art with a complete disclosure and description of how to make and use the present invention, and are not intended to limit the scope of the claims nor are they intended to represent that the experiments below are all or the only experiments performed. Those of skill in the art will readily recognize a variety of noncritical parameters that could be changed or modified to yield essentially similar results. Efforts have been made to ensure accuracy with respect to numbers used (e.g. amounts, dimensions, etc.) but some experimental errors and deviations should be accounted for.

Materials and Methods

Brain tissue from HAND and non-HAND patients was collected at autopsy with informed consent at different geographical locations (Texas, New York, San Diego and Los Angeles) by the National NeuroAIDS Tissue Consortium (Gelman B B, et al. 2013; J Acquir Immune Defic Syndr. 2013; 62(5):487-95; Gelman B B et al. 2012; PLoS One. 2012; 7(9):e46178). The use of autopsied brain tissues (Protocol number 2291) was approved by the University of Alberta Human Research Ethics Board (Biomedical) and written informed consents from all participants were signed before or at the collection times. The protocols for obtaining post-mortem brain samples comply with all federal and institutional guidelines with special respect for the confidentiality of the donor's identity. Blood for isolation of human monocyte-derived macrophages was obtained from healthy volunteers. Donors were first informed of potential risks and benefits prior to obtaining oral consent. Each donor was assigned an anonymized research number that was documented in a confidential file. The ethics protocol number for collection of blood from volunteers is Pro00041844.

MicroRNA Extraction from Human Brain Tissue

Neocortical brain tissue samples from midfrontal gyrus were excised from fresh-frozen brain slices and shipped in dry ice to the Laboratory for Neurological Infection and Immunity Brain Bank at University of Alberta. Samples were stored at −80° C. until total RNA extraction including microRNAs (miRNAs) was performed as follows. Briefly, ~100 mg/sample of autopsy-derived brain tissue was aseptically collected using sterile instruments into a 2 ml Lysing Matrix tube (MP Biomedicals, Santa Ana, CA, USA). Tissue samples were homogenized in a FastPrep-24 tissue homogenizer (MP Biomedicals, Santa Ana, CA, USA) after adding 1 ml of Trizol reagent (Invitrogen Carlsbad, CA, USA). Chloroform (200 µl) was added to each homogenate which was then centrifuged 12,000×g for 15 minutes at 4° C. The aqueous phase was collected and extraction followed as indicated in the manufacturer's manual (Qiagen, Catalog no. 217004).

MicroRNA Microarray and Statistics Analyses

Affymetrix miRNA 3.0 GeneChips were used for miRNA analyses. This microarray chip provides comprehensive coverage for mature human miRNAs (1733 probes) and pre-miRNAs (1658 probes). The Affymetrix® FlashTag™ Biotin highly sensitive and reproducible (HSR) RNA Labelling kit was used to label RNA samples for analysis. Equal concentrations of total RNA including microRNAs (800-1000 ng) were poly-A tailed as specified by the manufacturer (Affymetrix) followed by biotin-HSR ligation. Next, samples were treated with T4 DNA ligase before they were hybridized to Affymetrix miRNA 3.0 GeneChip arrays at 48° C. for 16 hours. Arrays were then stained and washed on an Affymetrix GeneChip Fluidics 450 following manufacturer's protocol and then scanned with an Affymetrix GeneChip Scanner 3000 7G System.

Genespring (version 12.6) software (Agilent Technologies) was used to normalize the data and identify differentially expressed miRNAs. The normalization in this software is based on the Robust Multi-array Average (RMA) algorithm, in which data are background-corrected, log 2 transformed and quartile normalized. To identify differentially expressed miRNAs, the median of each probe set in the HAND or nonHAND patients was calculated and the non-parametric test Mann-Whitney unpaired test was applied. To select for differentially expressed miRNAs in this analysis, a cut-off fold change (≥1.5) in relative miRNA abundance and a p value of <0.05 was considered statistically significant.

Prediction of microRNA Targets

Three different bioinformatics algorithms (miRDB; Diana-microT-CDS; and TargetScanHuman v6.2) were used to predict the potential targets of differentially expressed miRNAs. Only mRNA targets that were predicted by at least two of the three algorithms were investigated further.

Reagents

Complete™ EDTA-free protease inhibitor cocktail (Roche Diagnostics (Laval, Quebec, Canada); ProLong Gold anti-fade reagent with 4,6-diamidino-2-phenylindole (DAPI), SlowFade® Gold reagent mounting media, cell culture media DMEM, RPMI 1640, and fetal bovine serum (FBS) from Invitrogen (Carlsbad, CA) were purchased from the indicated suppliers. Lipofectamine 2000 and Lipofectamine RNAiMAX were purchased from Invitrogen (Carlsbad, CA); Per-Fectin transfection reagent was from Genlantis (San Diego, CA). miRIDIAN microRNA mimics including human hsa-miR-500a-5p, hsa-miR-34c-3p, hsa-miR-93-3p, hsa-miR-381-3p; miRIDIAN microRNA Mimic Negative Control #1 and miRIDIAN microRNA mimic mouse mmu-miR-344-3p; miRIDIAN microRNA inhibitors including human hsa-miR-500a-5p-Hairpin Inhibitor, hsa-miR-34c-3p-Hairpin Inhibitor, hsa-miR-93-3p-Hairpin Inhibitor and hsa-miR-381-3p-Hairpin Inhibitor were purchased from GE Healthcare Dharmacon Inc. (Lafayette, CO). MGC human PEX2 (Clone ID: 3347824), PEX7 (Clone ID: 5176358), PEX11B (Clone ID: 3866690), and PEX13 (Clone ID: 6285875) sequence-verified full-length cDNA clones were purchased from GE Healthcare Dharmacon Inc. (Lafayette, CO). Reagents for purification and quantitation of miRNAs including MiRNeasy Mini kit, miScript PCR Starter kit, miScript II RT kit, and miScript SYBR® Green PCR kit were purchased from Qiagen (Toronto, ON).

Antibodies

Mouse monoclonal antibodies against the peroxisomal membrane protein PMP70 (Sigma, St. Louis, MO), HIV-1 p24 (Abcam, Cambridge, MA), and beta-actin (Abcam, Cambridge, MA) were purchased from indicated suppliers. Rabbit polyclonal antibodies to PEX7, PEX11B, PEX13, PEX19 and catalase were from Abcam (Cambridge, MA); Rabbit polyclonal antibody to PEX2 (PXMP3) was purchased from Pierce (Rockford, IL); Rabbit polyclonal antibody to thiolase (ACAA1) was from MyBioSource (San Diego, CA); Rabbit polyclonal antibody to the tri-peptide SKL were produced following protocols as previously described (Aitchison J D et al. 1992; Yeast. 1992; 8(9):721-34).

Donkey anti-mouse IgG conjugated to Alexa Fluor 680, goat anti-rabbit IgG conjugated to Alexa Fluor 680, donkey anti-mouse IgG conjugated to Alexa Fluor 488, donkey anti-rabbit IgG conjugated to Alexa Fluor 488, and donkey anti-mouse IgG conjugated to Alexa Fluor 546 were purchased from Invitrogen (Carlsbad, CA).

Isolation and Culture of Monocyte-Derived Macrophages (MDMs)

The buffy coats used for PBMC isolation were derived from healthy volunteer blood donors. Human monocytes were isolated using Histopaque® (Sigma-Aldrich). Briefly, the blood was diluted 1:1 with phosphate-buffered saline (PBS), placed under a layer of Histopaque® and centrifuged for 22 min at 1800 rpm in a clinical centrifuge. Cells from the interphase layer were harvested, washed twice with serum-free RPMI, and then resuspended in RPMI1640 with 15% FBS, 1% penicillin and streptomycin (Invitrogen, Carlsbad, CA). The cells (2-4 million per well) were then seeded in 6-well plates that were pre-coated with poly-L-ornithine (Sigma, St. Louis, MO). After 4 hours, the cells were washed three times with warm RPMI medium before adding 2 mL Differentiation medium (25 ng/mL macrophage colony-stimulatory factor (M-CSF) (Sigma, St. Louis, MO) in RPMI containing 2 mM L-glutamine, 1% penicillin and streptomycin and 15% FBS) to each well. Cells were incubated for 7 days in this media (with media changes every 3 day) to allow differentiation of MDMs.

Cell Culture, Transfection and Virus Infection

A549 and HEK293T cells from the American Type Culture Collection (Manassas, VA) were cultured in DMEM (Invitrogen) containing 10% heat-inactivated FBS, 4.5 g/liter D-glucose, 2 mM glutamine, 110 mg/liter sodium pyruvate at 37° C. in a 5% $CO_2$ atmosphere. Hela CD4+ (clone 1022) cells (NIH AIDS Reagent Program, Germantown, MD) were cultured in RPMI 1640 supplemented with 10% FBS and 1.0 mg/ml G418 (Geneticin, Gibco).

A549 and HEK293T cells were transfected with the expression plasmids using Lipofectamine 2000 (Invitrogen) and PerFectin (Genlantis) respectively as described by the manufacturers. When using miRNA mimics or anti-miRs, cells were transfected with Lipofectamine RNAiMAX (Invitrogen). HIV-1 infection in Hela CD4+ cells (pYU2, MOI=10) or primary monocyte-derived macrophages (pYU2, MOI=2) was performed under biosafety CL-3 conditions.

Reporter Constructs for miRNA Target Validation

To test whether miRNA mimics could silence predicted target genes, the entire 3'-untranslated regions (UTRs) of selected target genes were subcloned into the luciferase expression vector pMIR-REPORT-Luc (Ambion). Plasmids were constructed using polymerase chain reaction (PCR) and standard subcloning techniques. Sequence-verified full-length cDNAs of each PEX gene were used as templates to amplify the 3'-UTRs by PCR with primers listed in FIG. 16. The resulting PCR products were digested with HindIII and then subcloned immediately downstream of the luciferase cassette contained in the reporter plasmid pMIR-REPORT-Luc. The orientation of each 3'-UTR insert was determined by endonuclease digestion and all constructs were then verified by DNA sequencing.

Luciferase Reporter/β-Galactosidase Assay for miRNA Target Validation

The pMIR-REPORT™ miRNA Expression Reporter System (Ambion) was used to validate miRNA targets and conduct quantitative evaluations of miRNA function. The assay employs an experimental firefly luciferase-based reporter vector and an associated β-gal reporter control plasmid (pMIR-REPORT β-gal). The pMIR-REPORT Luciferase plasmid contains a firefly luciferase reporter gene upstream of a multiple cloning site for insertion 3'UTRs that contain predicted miRNA-binding sites in its 3'-UTR. By cloning a cDNA fragment with a miRNA target sequence into the pMIR-REPORT plasmid, expression of the luciferase reporter can be negatively regulated by miRNAs. β-galactosidase expression from the pMIR-REPORT β-gal was used to normalize variability due to differences in cell viability and/or transfection efficiency.

After 48 hours, lysates prepared from HEK293T cells transfected with pMIR-REPORT-Luciferase containing 3'-UTRs from different PEX genes (PEX2, PEX7, PEX11B or PEX13), pMIR-REPORT β-gal together with miRNA mimics were subjected to luciferase and β-gal assays. Briefly, growth medium was removed and cells were rinsed once with PBS. A minimal volume of 1× Reporter Lysis Buffer (RLB) (Promega) was added to each well and then the plates were rocked for several times to ensure complete coverage of the cells with RLB. Cells scraped from the wells were transferred to microcentrifuge tubes and placed on ice for 10 minutes. The microcentrifuge tubes were vortexed for 10-15 seconds and then centrifuged at 12,000×g for 2 minutes at 4° C. The supernatant/cell lysates were transferred to new tubes and used immediately for assays or stored at −70° C.

For luciferase assays, 20 µl of cell lysate and 100 µl of Luciferase Assay Reagent (Promega) were mixed in microcentrifuge tubes and luminescence was measured using a model Synergy 4 Luminometer (BioTek). For β-Galactosidase assays, 150 µl of cell lysate (2:1 dilution to 1×RLB) was mixed with 150 µl of Assay 2× Buffer (Promega) and then incubated at 37° C. for 30 minutes or until a faint yellow color had developed. The reactions were terminated with 1M sodium carbonate (500 µl) after which the absorbances were read at 420 nm. The relative luciferase activity was expressed as a ratio of luciferase activity to β-gal activity.

Immunoblotting

Transfected or HIV-infected cells grown in 6-well plates were washed twice with cold PBS on ice and then lysed with RIPA buffer (50 mM Tris-HCl pH 7.4, 150 mM NaCl, 1% Triton x-100, 1% Sodium deoxycholate, 0.1% SDS, 1 mM EDTA) containing a cocktail of protease inhibitors. Lysates were incubated on ice for 30 minutes and then centrifuged at 14,000×g for 15 minutes at 4° C. after which protein concentrations in the supernatants were quantified using a Pierce BCA protein assay kit (Thermo Scientific). Equivalent amounts of total protein (20 µg) were resolved by SDS-PAGE and then transferred to polyvinylidene difluoride membranes (EMD Millipore) membranes for immunoblotting.

Membranes were blocked with 3% skim milk powder in PBS containing 0.1% Tween 20 (PBS-T) and then incubated overnight at 4° C. or 3 hours at room temperature with appropriate primary antibodies diluted in 3% milk-PBS-T. After washing three times with PBS-T for 10 minutes each, fluorescent secondary antibodies (donkey anti-mouse IgG conjugated to Alexa Fluor 680 or goat anti-rabbit IgG conjugated to Alexa Fluor 680) diluted in PBS-T were used to detect the primary antibodies. After 1-hour incubation with the secondary antibodies, membranes were washed three times with PBS-T for 10 minutes each. Detection and quantification of the protein signals in the immunoblots was performed using a Licor Odyssey Infrared Imaging System (Lincoln, Neb.) using the protocol posted at http://biosupport.licor.com. Relative levels of PMP70, PEX2, PEX7, PEX11B, PEX13, PEX19, and catalase (normalized to actin) were determined using Odyssey Infrared Imaging System 1.2 Version software.

Confocal and Super-Resolution Microscopy

Hela CD4+ and A549 cells grown on coverslips were processed respectively for confocal or super-resolution microscopy at 48h post-transfection or infection. Cells were washed in PBS containing 0.5 mM $Ca^{2+}$ and 1.0 mM $Mg^{2+}$ and then fixed with 3% paraformaldehyde (for confocal imaging) or 1.5% electron microscopy grade paraformaldehyde (for super-resolution imaging) for 30 min at room temperature. Samples were then quenched with 50 mM $NH_4Cl$ in PBS for 5 minutes at room temperature, washed three times with PBS, and then permeabilized with 0.2% Triton-X-100 for 5 min. Incubations with primary antibodies diluted (1:500-1000) in blocking buffer (3% BSA in PBS) were performed at room temperature for 2 hours followed by three washes in PBS containing 0.1% BSA. Samples were then incubated with secondary antibodies in blocking buffer for 1 hour at room temperature followed by three washes in PBS containing 0.1% BSA. Secondary antibodies were donkey anti-mouse/rabbit IgG conjugated to Alexa Fluor 488 and donkey anti-mouse IgG conjugated to Alexa Fluor 546 (Invitrogen).

For confocal microscopy, coverslips were mounted onto microscope slides using ProLong Gold antifade reagent with DAPI (Invitrogen), and samples were examined using an Olympus 1×81 spinning disk confocal microscope equipped with a 60×/1.42 oil PlanApo N objective. Confocal images were acquired and processed using Volocity 6.2.1 software.

For super-resolution microscopy, coverslips were mounted on slides pre-cleaned with acetone and ethanol using SlowFade® Gold reagent mounting media (Invitrogen). Images were acquired using a DeltaVision OMX V4 structured illumination microscope (Applied Precision, GE) equipped with a 60×1.42 oil PSF (PlanApo N) objective and immersion oil N=1.514~1.516. Images were analyzed using Volocity 6.2.1 software.

Quantification of Peroxisomes

Z-stack images acquired using a confocal microscope were exported from Volocity 6.2.1 as an OEM.tiff file. The exported images were then processed using Imaris 7.2.3 software (Bitplane). Peroxisomes within polygonal areas that excluded the nucleus were quantified (quality and voxel). Within the selected regions, the absolute intensity/region volume of the peroxisomes were determined and then entered into a Microsoft Excel spreadsheet. The data were then analyzed using student's t-test.

Where indicated, 0.125 µm optical sections acquired using an Applied Precision OMX super resolution microscope (with a 60×/1.42 Oil lens and three CMOS cameras) were also analyzed. The raw data were processed using Deltavision OMX SI image reconstruction and registration software and the final images were imported into Volocity 6.2.1 software as .dv files for quantification. In each cell, peroxisomes were selected based on the absolute pixel intensity in the corresponding channel and their numbers and volumes were then determined. Only those SKL/PMP70-positive structures with volumes between 0.001 and 0.05 µm³ were included for measurement.

Immunohistochemistry and Histochemistry

Formalin-fixed paraffin-embedded human brain was processed and tissue sections (10 µm) were prepared and labeled according to procedures described previously [Walsh J G et al. 2014; Retrovirology 2014; 11:35; Aitchison J D et al. Yeast. 1992; 8(9):721-34; Power C et al. 1996; J Neurosci Res. 1996; 44(2):165-73]. Briefly, samples were deparaffinized by incubation for 1 hour at 60° C. followed by one 10 min and 2 five min incubations in xylene baths through decreasing concentrations of ethanol to distilled water. Antigen retrieval was performed by boiling in 10 mM sodium citrate (pH 6.0) 1 hr. Slides were blocked with HHFH buffer (1 mM HEPES buffer, 2% (v/v) horse serum, 5% (v/v) FBS, 0.1% (w/v) sodium azide in Hank's balanced salt solution (HBSS)) for 4 hrs at room temperature. Slides were stained with hematoxylin and eosin (H&E). In addition, serial brain sections were immuno-labelled with antibodies to host proteins Immunocytochemistry was performed with rabbit anti-Iba-1 (Wako Pure Chemical Industries Ltd., Osaka Japan), anti-thiolase or anti-PEX13 with appropriate secondary antibodies. For immunofluorescence studies, slides were incubated with a cocktail of rabbit anti-GFAP (DAKO, Carpenteria CA) or anti-Iba-1 (1:400) and anti-PEX13, overnight at 4° C. The primary antibodies were removed by three 5 min PBS washes and slides were incubated for three min in 0.22 micron filtered 1% (w/v) Sudan black in 70% ethanol and washed an additional 3 times in PBS. A cocktail of 1:500 Alexa 488 goat anti rabbit IgG, Alexa 568 goat anti mouse IgG for two hrs, washed 3 times in PBS stained with DAPI for 10 min, washed 3 times in PBS and mounted with Prolong gold antifade reagent. Slides were imaged with Wave FX spinning disc confocal microscope (Zeiss).

QPCR Analysis of miRNA Expression

Total RNA including small RNA from HIV-infected Hela CD4+ cells or primary MDMs was purified using the miRNeasy Mini Kit (Qiagen) according to the manufacturer's instructions. Mature miRNAs, certain small nucleolar RNAs and small nuclear RNAs (snoRNAs and snRNAs) were selectively reverse-transcribed into cDNA using miScript HiSpec buffer according to the instructions of miScript II RT Kit (Qiagen). Mature miRNAs, which are polyadenylated, were reverse transcribed into cDNA using oligo-dT primers. The oligo-dT primers included a 3' degenerate anchor and a universal tag sequence on the 5' end, allowing amplification of mature miRNA during the real-time PCR step.

The resulting cDNAs served as the template for real-time PCR analysis using miRNA-specific primers (forward primers, from IDT) and the miScript SYBR® green PCR kit (Qiagen), which contains the miScript universal primer (reverse primer) and QuantiTect SYBR green PCR master mix. The amplification cycles consisted of an initial activation step at 95° C. for 15 min, followed by 40 cycles of 15 s at 94° C., 30 s at 55° C. and 30 s at 70° C. Fluorescence data were collected during the 70° C. extension step. The miRNA targets and primers that were used in this study are listed in FIG. 16. As an internal control, levels of a small nuclear RNA RNU6B (a miScript PCR control provided in the miScript PCR starter kit (Qiagen)) were determined. Relative miRNA expression was normalized to RNU6B levels using the comparative cT ($\Delta\Delta$cT) method. All miRNA expression studies were conducted using a Mx3005P (Stratagen, LaJolla, CA) thermocycler.

Example 1: Brains of Patients with HIV-Associated Neurocognitive Disorder (HAND) Exhibit Distinct microRNA Profile Peroxisomes are ubiquitous and essential subcellular organelles responsible for the catabolism of fatty acids (beta oxidation), amino acids, reduction of free radicals such as hydrogen peroxide and the synthesis of plasmalogens. The latter is critical for myelin formation and brain development (Wanders R J and Waterham H R. Annu Rev Biochem. 2006; 75:2 95-332). Formation of peroxisomes requires multiple peroxin (PEX)-encoding genes and mutations result in devastating diseases that include defects in brain development (Weller S, et al. Annu Rev Genomics Hum Genet. 2003; 4: 165-211; Trompier D, et al. Brain peroxisomes. Biochimie. 2014; 98: 102-10). In addition to their roles in cellular lipid metabolism and brain development and function, peroxisomes serve as signaling platforms in antiviral defense (Dixit E, et al. Cell. 2010; 141(4):668-81) further underlying their importance in human health. Activation of peroxisomal-mitochondrial antiviral signaling protein (MAVS) during RNA virus infections leads to the production of type III interferon (IFN) as well as IFN-stimulated genes (ISGs) (Dixit E, et al, 2010, supra; Odendall C, et al. Nature immunology. 2014; 15(8):717-26). Peroxisomes play a role in sensing the HIV-1 genomic RNA (Berg R K, et al. PLoS One. 2012; 7(1):e29291) and stimulation of peroxisome proliferator-activated receptor alpha by fenofibrate impairs replication of HIV-1 and flaviviruses in vivo (Sehgal N, et al. PloS one. 2012; 7(4):e35427; Skolnik P R, et al., 2002; 31(1):1-10).

The development of HAND was dependent on multiple factors including aberrant expression of host-encoded miRNAs. To determine whether there were signature miRNA expression patterns common to HAND patients, a well-defined patient cohort was examined, focusing on miRNA profiles in brain tissue from HIV/AIDS patients with HAND (n=20; with encephalitis, n=10 and without encephalitis, n=10) to HIV/AIDS patients without HAND or encephalitis (n=10). To ensure there were sufficient patients in each group and because there were no significant differences in miRNA expression between the two HAND groups, the results from each HAND group were pooled. It was found that expression of 17 miRNAs (FIG. 1 and FIGS. 12A-12B) was consistently dysregulated in the HAND samples. Twelve of the miRNAs were upregulated and five were down-regulated by at least 1.5 fold (p<0.05).

FIG. 1. Distinct miRNA profile in brains of HAND patients. 12 up-regulated and 5 down-regulated miRNAs were identified in brains of HAND (n=20) compared to nonHAND (n=10) patients based on Gene Spring RMA normalization method. miRNAs that were down-regulated (B) cluster together while up-regulated miRNAs (A) form another cluster. Also, those from HAND and non-HAND patient samples form separate clusters.

Example 2: Several miRNAs That are Deregulated in Hand Patients Target mRNAs Encoding Peroxisomal Proteins To understand the potential effects of the differentially expressed miRNAs in pathogenesis of HAND and/or HIV-1 biology, it was important to elucidate their cellular targets. Three bioinformatics algorithms (miRDB, DIANA, and TargetScan) were used to predict potential targets of the 17 differentially expressed miRNAs. The first focus was on targets that were predicted by at least two of the three algorithms. In keeping with the notion that a single miRNA can affect expression of dozens of mRNAs, hundreds of potential targets were identified. Some of the highest-ranking candidates are listed in FIGS. 15A-15B. Interestingly, four of the up-regulated miRNAs (miR-500a-5p, miR-34c-3p, miR-93-3p, and miR-381-3p) were predicted to target mRNAs encoding the peroxins PEX2, PEX7, PEX11B and PEX13. These proteins play different but critical roles in biogenesis of peroxisomes. Specifically, PEX2 and PEX13 are required for import of peroxisomal matrix proteins; PEX11B facilitates peroxisomal division and proliferation and PEX7 functions as a receptor for the import of peroxisomal matrix proteins with type 2 targeting motifs (Fujiki Y et al. 2014; Front Physiol. 2014; 5:307).

Figure 2:
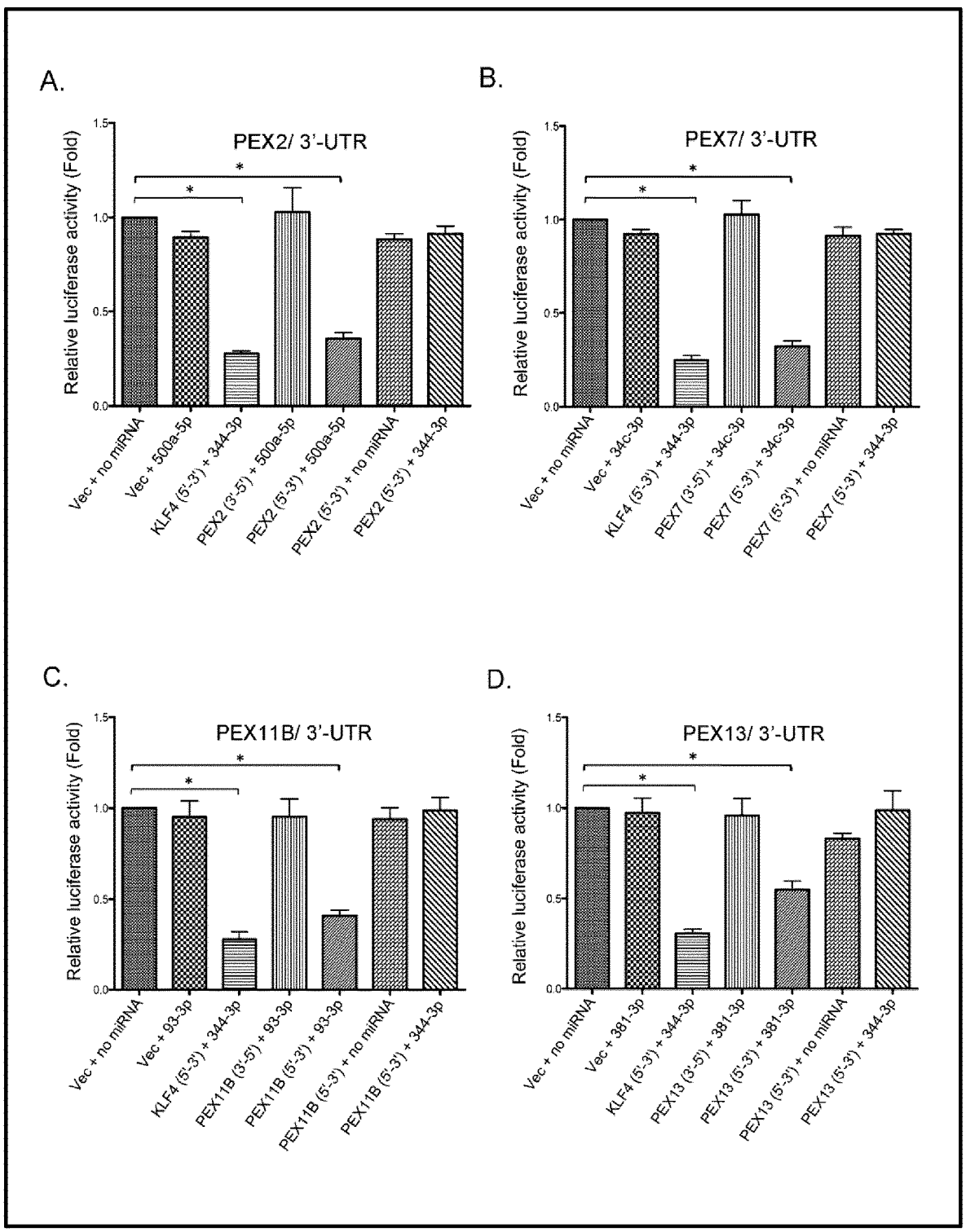
FIG. 2 shows a subset of HAND-associated miRNAs that negatively regulate expression of PEX mRNAs (See panels A-D).

Peroxisomes have recently been linked to antiviral defense (Wanders R J et al. 2006; 75:295-332; Weller S, et al. 2003; Annu Rev Genomics Hum Genet. 2003; 4:165-211) and have long been known to contribute to neuroinflammation (Berger J et al. 2016; Biochim Biophys Acta. 2016; 1863(5):934-55). In most cases, miRNAs negatively regulate gene expression at the post-transcriptional level through binding to the 3'untranslated regions (UTRs) of mRNAs. Therefore, it was first determined whether miR-500a-5p, miR-34c-3p, miR-93-3p, or miR-381-3p affected expression of a reporter gene upstream from the 3'UTRs of PEX2, 7, 11B or 13 mRNAs (FIG. 2). The pMIR-REPORT™ miRNA expression reporter system consists of a firefly luciferase reporter vector (for 3'-UTR cloning) and a β-gal reporter control plasmid (for normalization based on potential differences in cell viability and transfection efficiency). Several controls were included for each experiment. For example, miR-344-3p targets the 3'UTR of KLF4 (Lin C. C., et al.; Mol Cell Biol. 2011; 31(12):2513-27) and therefore, this miRNA was used as the positive control. For negative controls, cassettes encoding the 3'-UTRs for the PEX genes were also cloned into the reporter vector in the opposite direction.

Expression of luciferase activity under the control of PEX2, PEX7, PEX11B, or PEX13 UTRs was inhibited by 50-70% in cells transfected with miR-500a-5p, miR-34c-3p, miR-93-3p or miR-381-3p respectively (FIG. 2). Conversely, these miRNAs did not affect luciferase activity when the orientations of PEX 3'UTRs were reversed. Together, these data indicate that four of the miRNAs upregulated in the brains of HAND patients efficiently suppress expression of PEX mRNAs.

FIG. 2. A subset of HAND-associated miRNAs negatively regulate expression of PEX mRNAs. HEK293T cells were co-transfected with luciferase reporter plasmids (pMIR-REPORT-Luciferase) containing 3'-UTRs from PEX2 (Panel A), PEX7 (Panel B), PEX11B (Panel C) and PEX13 (Panel D) in forward (5'-3') or reverse orientations (3'-5'), a transfection control reporter plasmid (pMIR-REPORT-β-gal) and miRNA mimics for miR-500a-5p, miR-34c-3p, miR-93-3p, miR-381-3p and miR-344-3p. After 48 hours, cell lysates were subjected to luciferase and β-gal assays. N=3 Bars represent standard error of the mean. Key to plasmids: Vec=pMIR-REPORT-Luciferase; KLF4=pMIR-REPORT-Luciferase with 3' UTR of KLF4 downstream from luciferase cassette; PEX2=pMIR-REPORT-Luciferase with 3' UTR of PEX2 downstream from luciferase cassette; PEX7=pMIR-REPORT-Luciferase with 3' UTR of PEX7 downstream from luciferase cassette; PEX11B=pMIR-REPORT-Luciferase with 3' UTR of PEX11B downstream from luciferase cassette; PEX13=pMIR-REPORT-Luciferase with 3' UTR of PEX13 downstream from luciferase cassette. As a positive control, miR-344-3p is shown to downregulate expression of luciferase under the control of the 3'UTR of KLF4 mRNA.

Example 3: miR-500a-5p, miR-34c-3p, miR-93-3p, and miR-381-3p Significantly Decrease Levels of Peroxisomal Proteins The next focus was on determining whether expression of the PEX mRNA-targeting miRNAs reduced levels of peroxisomal proteins Immunoblotting was used to quantify the relative levels of peroxisomal proteins in cells transfected with mimics of miR-500a-5p, miR-34c-3p, miR-93-3p, miR-381-3p or a non-silencing miRNA (miR-NS). Data in FIG. 3, Panel A show that compared to mock and miR-NS-transfected cells, miR-500a-5p, miR-34c-3p, miR-93-3p and miR-381-3p significantly decreased the levels of peroxisomal proteins albeit to different extents. Specifically, miR-500a-5p, which targets PEX2 mRNA (FIG. 2), reduced levels of PEX2 protein by 35%. Interestingly, PEX7 and PEX11B protein levels were 70% and 69% lower respectively in cells transfected with miR-500a-5p. Similarly, the PEX13-targeting miR-381-3p decreased expression levels of four peroxisomal proteins including PMP70 (a peroxisomal membrane protein), PEX7, PEX13, and PEX2. Unexpectedly, transfection of cells with miR-34c-3p or miR-93-3p did not significantly impact PEX7 or PEX11B protein levels respectively. However, miR-34c-3p expression resulted in loss of PMP70 and PEX13 proteins. Expression of PEX13 was only slightly decreased by miR-93-3p. Levels of catalase, a peroxisomal matrix protein, were unaffected by expression of the four miRNAs.

There are a number of scenarios in which a single miRNA can affect expression of multiple Pex gene products. One possibility is that miR-500a-5p, miR-381-3p and/or miR-34c-3p inhibit translation of multiple mRNAs that encode PEX proteins. Indeed, miRNAs that target components of a cellular pathway can be synthesized as a common transcript that contains multiple primary miRNAs (Ryazansky S S et al. 2011; BMC Genomics. 2011; 12:371). However, a search of the miRBase database indicated that genes encoding miR-500a-5p, miR-34c-3p, miR-93-3p, and miR-381-3p are located on different chromosomes. The initial miRNA target search using miRDB, DIANA, and TargetScan did not indicate that multiple PEX mRNAs are targeted by miR-500a-5p, miR-34c-3p, miR-93-3p, or miR-381-3p. Finally, to experimentally determine if any of these miRNAs could target more than one PEX gene, the luciferase-based reporter assay was employed, as described above. Data presented in FIG. 9 confirmed that the miRNAs only regulated expression of luciferase under the control of 3'UTRs from their predicted PEX mRNA targets. Specifically, miR-500a-5p, miR-34c-3p, miR-93-3p and miR-381-3p downregulated expression of PEX2, PEX7, PEX11B and PEX13 3'UTRs respectively.

Figure 13:
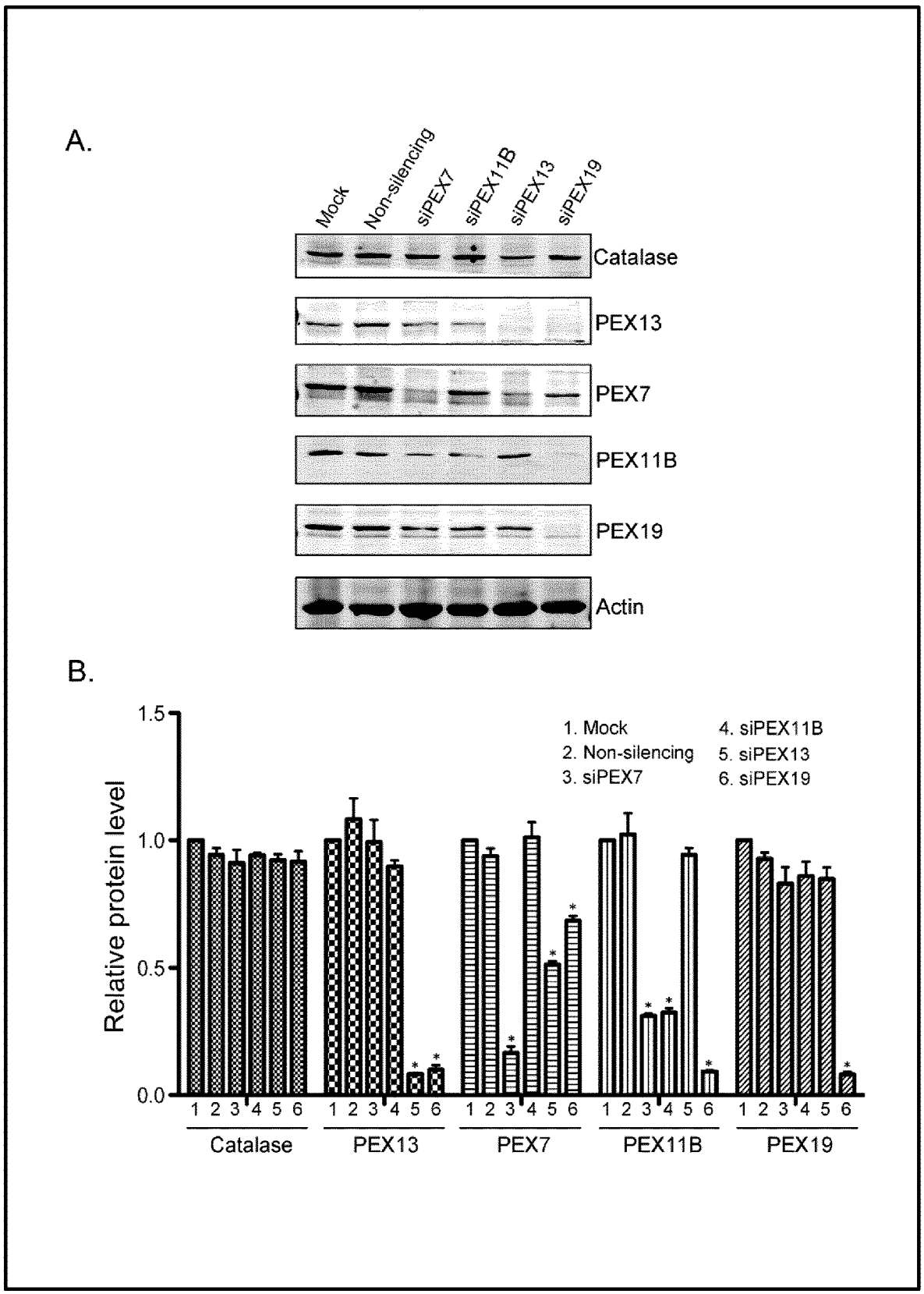
FIG. 13 shows that knockdown of one PEX protein can affect the stabilities of other PEX proteins (panels A-B).

SiRNAs were also used to determine if loss of PEX2, PEX7, PEX11B or PEX13 led to decreased levels of other PEX proteins. Unlike miRNAs, which are inherently degenerate with respect to mRNA targets, siRNAs are perfectly complementary to their mRNA targets. siRNAs against PEX2, PEX7, PEX11B or PEX13 were transfected into HEK293T cells and levels of proteins were determined by immunoblotting (FIG. 13). These experiments showed that targeted knockdown of a single PEX protein can result in concomitant loss of other PEX proteins. For example, siRNAs against PEX7 not only reduced the level of PEX7 protein, but PEX11B was also markedly lower. Similarly, a PEX13-specific siRNA reduced the levels of PEX13 and PEX7 proteins. Finally, downregulation of the multifunctional peroxisome biogenesis factor PEX19 using siRNA, effectively reduced levels of PEX19, PEX7, PEX11B and PEX13 proteins.

Figure 3:
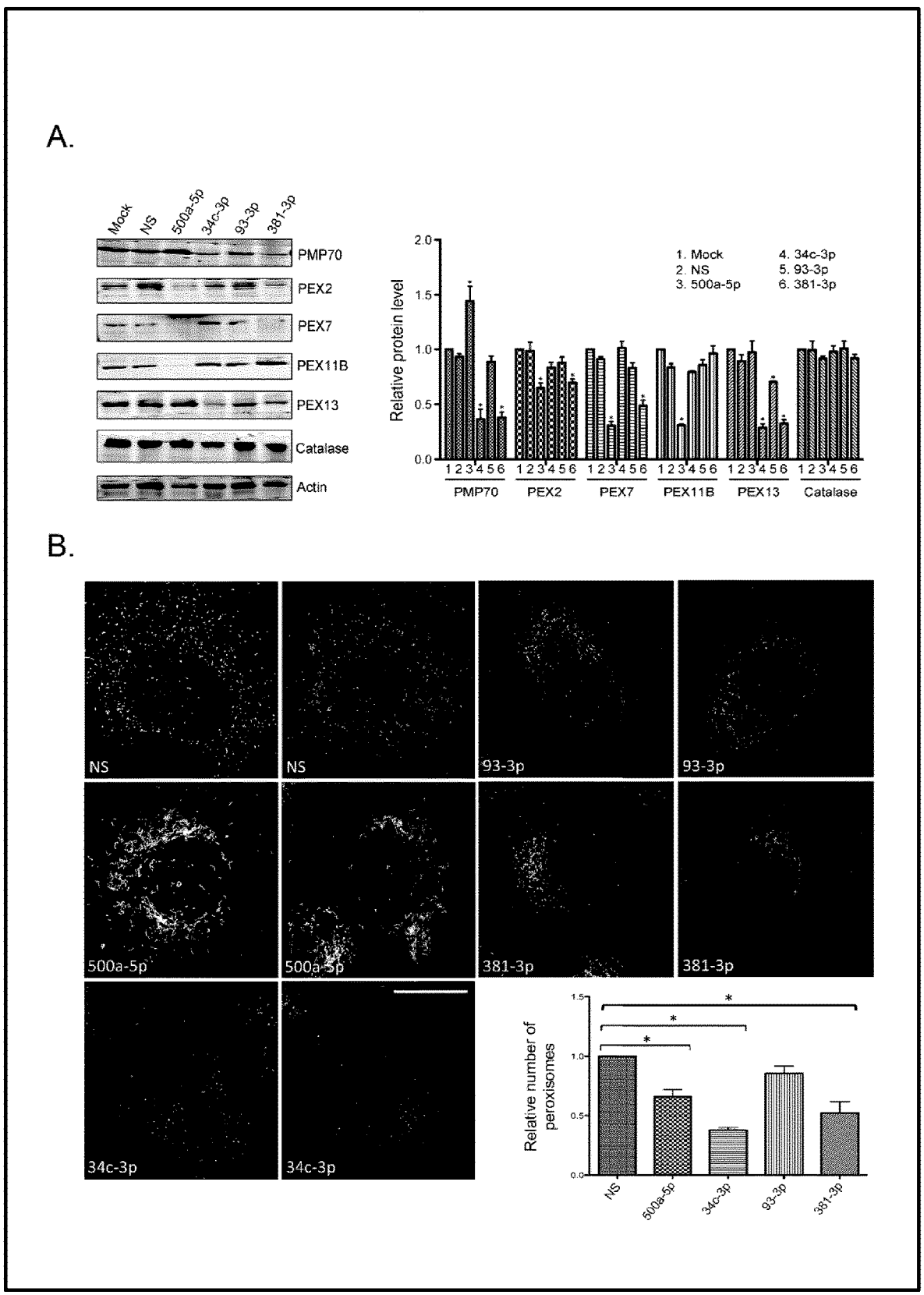
FIG. 3 shows a subset of HAND-associated miRNAs reduces expression of peroxisomal proteins and alters peroxisome abundance and/or morphology (See panels A-B).

FIG. 3. A subset of HAND-associated miRNAs reduces expression of peroxisomal proteins and alters peroxisome abundance and/or morphology. Panel A shows that A549 cells were transfected with mimics (30 nM) for miR-NS, miR-500a-5p, miR-34c-3p, miR-93-3p or miR-381-3p. Forty-eight hours later, cell lysates were subjected to immunoblot analyses. PMP70 and actin were detected using primary mouse monoclonal antibodies and secondary donkey anti-mouse IgG conjugated to Alexa Fluor 680. PEX2, PEX7, PEX11B, PEX13 and catalase were detected using primary rabbit antibodies and secondary goat anti-rabbit IgG conjugated to Alexa Fluor 680. Relative peroxisomal protein levels (normalized to actin) in mock- and miRNA-transfected cells from three independent experiments are shown. Bars represent standard error of the mean. Panel B shows that A549 cells were transfected with 30 nM of mimics for miR-NS, miR-500a-5p, miR-34c-3p, miR-93-3p or miR-381-3p for 38 hours after which they were processed for super resolution microscopy. Peroxisomes were identified using a mouse monoclonal antibody to PMP70 and donkey anti-mouse IgG conjugated to Alexa Fluor 488. Nuclei were stained with DAPI. Images were acquired and reconstructed using a DeltaVision OMX structured illumination microscope. Size bar is 10 µM. The relative numbers of peroxisomes in cells transfected with each miRNA were determined using Volocity image analyses software from three independent experiments (minimum of 20 cells). Bars represent standard error of the mean. *, p<0.05.

Figure 12:
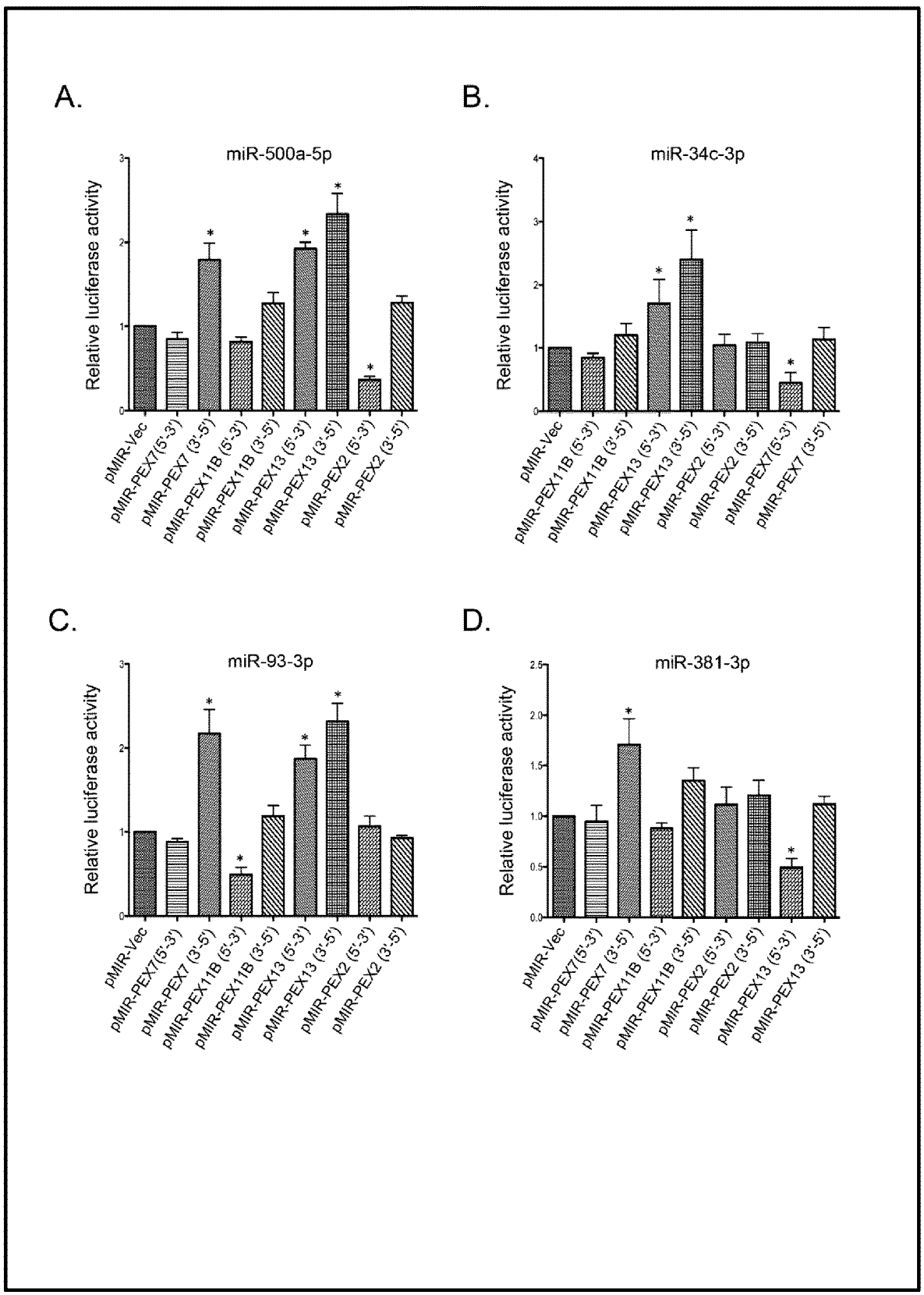
FIG. 12 shows specificity of the HAND-associated miRNAs (panels A-D).

FIG. 12. Specificity of the HAND-associated miRNAs. HEK293T cells were co-transfected with luciferase reporter plasmids (pMIR-REPORT-Luciferase) containing 3'-UTRs from PEX2, PEX7, PEX11B and PEX13) in forward (5'-3') or reverse orientations (3'-5'), a transfection control reporter plasmid (pMIR-REPORT-β-gal) and miRNA mimics for miR-500a-5p (Panel A), miR-34c-3p (Panel B), miR. After 48 hours, cell lysates were subjected to luciferase and β-gal assays. N=3. Error bars represent standard error of the mean. From the data it can be see that each miRNA only suppresses one reporter construct. Specifically: miR-500a-5p suppresses expression of PEX2; miR34c-3p suppresses expression of PEX7; miR-93-3p (Panel C) suppresses expression of PEX11B; and miR-381-3p (Panel D) suppresses expression of PEX13.

Key to plasmids: pMIR-Vec=pMIR-REPORT-Luciferase; pMIR-KLF4=pMIR-REPORT-Luciferase with 3' UTR of KLF4 downstream from luciferase cassette; pMIR-PEX2=pMIR-REPORT-Luciferase with 3' UTR of PEX2 downstream from luciferase cassette; pMIR-PEX78=pMIR-REPORT-Luciferase with 3' UTR of PEX7 downstream from luciferase cassette; pMIR-PEX11B=pMIR-REPORT-Luciferase with 3' UTR of PEX11B downstream from luciferase cassette; pMIR-PEX13=pMIR-REPORT-Luciferase with 3' UTR of PEX13 downstream from luciferase cassette.

FIG. 13. Knockdown of one PEX protein can affect the stabilities of other PEX proteins. Individual siRNAs against PEX7, PEX11B, PEX13 or PEX19 were transfected into HEK293T cells for 48 hours and then levels of peroxisomal proteins were determined by immunoblotting (Panel A) with corresponding antibodies. The average relative levels of peroxisomal proteins (compared to actin) from 3 independent experiments are shown in Panel B. Error bars represent standard error of the mean.

Example 4: Expression of miR-500a-5p, miR-34c-3p and miR-381-3p Dramatically Affects Peroxisomes Next, expression of miR-500a-5p, miR-34c-3p, miR-93-3p, and miR-381-3p was examined to see how the expression affected peroxisomes. Super-resolution microscopy was used to analyze the morphology, distribution and numbers of peroxisomes in miRNA-transfected cells. Peroxisomes were identified using an antibody to PMP70, a peroxisomal membrane protein involved in membrane assembly (Gartner J et al. 1992; Nat Genet. 1992; 1(1):16-23). Cells transfected with a non-silencing miRNA (miR-NS) contained hundreds of PMP70-positive puncta throughout the cytoplasm (FIG. 3, Panel B). While the number of peroxisomes was significantly reduced by expression of miR-500a-5p (which targets PEX2), most striking was the change in morphology and PMP70 staining of the peroxisomes. Specifically, miR-500a-5p over-expression resulted in enlargement and elongation of peroxisomes. PEX2, an E3 ubiquitin ligase that targets PMP70 (Sargent G et al. 2016; J Cell Biol. 2016; 214(6): 677-90) could certainly explain the increased levels of PMP70 protein (FIG. 3, Panel A) and intensity of anti-PMP70 staining in miR-500a-5p over-expressing cells (FIG. 3, Panel B).

It is also important to point out that PEX11B is required for peroxisome fission (Fujiki Y et al. 2014; Front Physiol. 2014; 5:307) and as such, loss of PEX11B in miR-500a-5p expressing cells would therefore be expected to result in decreased fission of peroxisomes and concomitant lengthening and enlargement of these organelles. Unexpectedly, the effect of miR-93-3p (which targets PEX11B) on peroxisomes was minimal. Despite the evidence showing that the 3'UTR of PEX11B is targeted by this miRNA (FIG. 2), PEX11B protein levels were not significantly affected by over-expression of a miR-93-3p mimic (FIG. 3, Panel A). Finally, it can be seen that expression of miR-34c-3p and miR-381-3p reduce peroxisome numbers by 65% and 45% respectively (FIG. 3, Panel B). Notably, this is consistent with the immunoblot data in FIG. 3, Panel A showing that levels of PMP70 protein were reduced by expression of miR-34c-3p and miR-381-3p.

Figure 4:
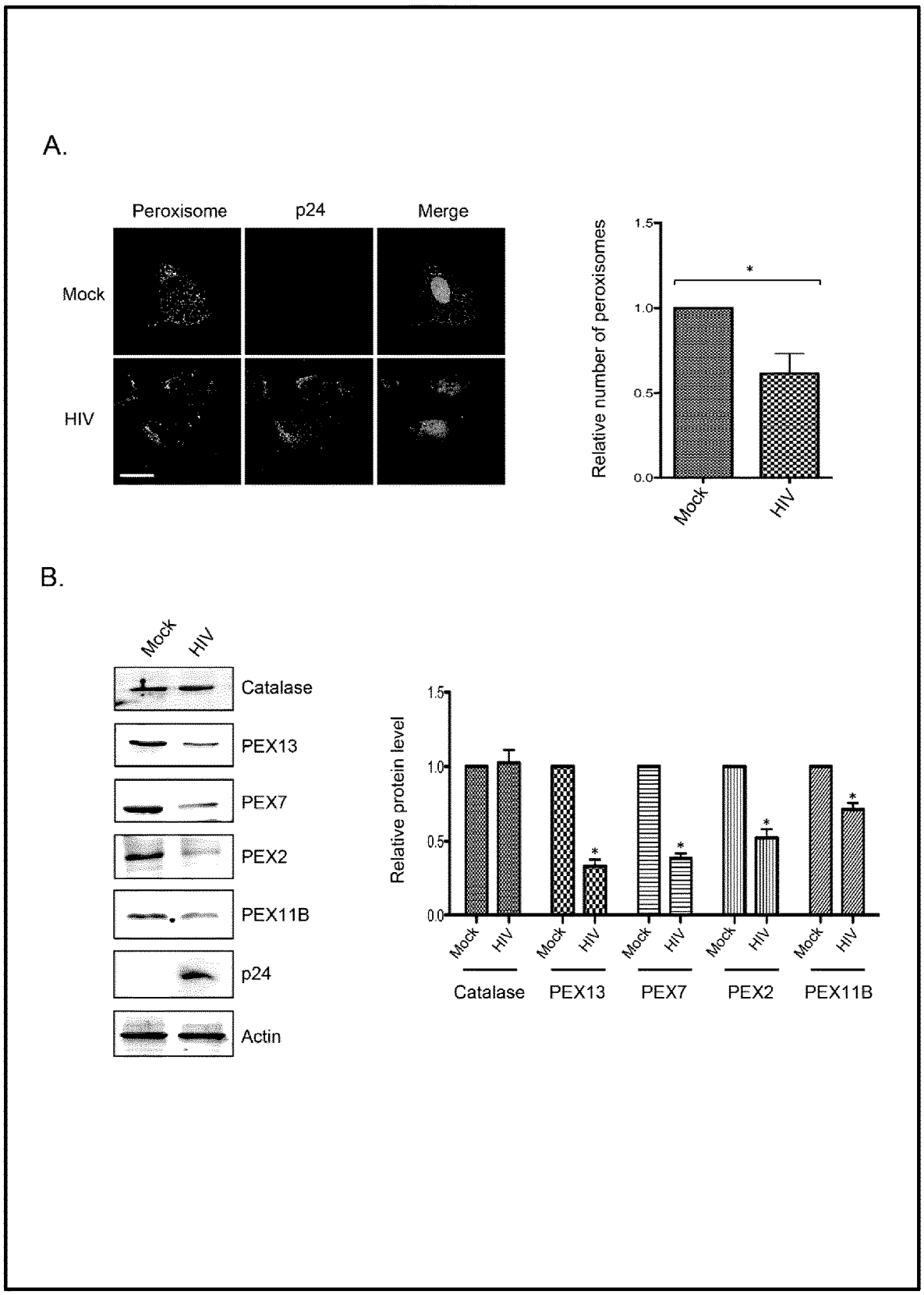
FIG. 4 shows that HIV-1 infection causes loss of peroxisomal proteins and reduces the abundance of peroxisomes (See panels A-B).
Figure 14:
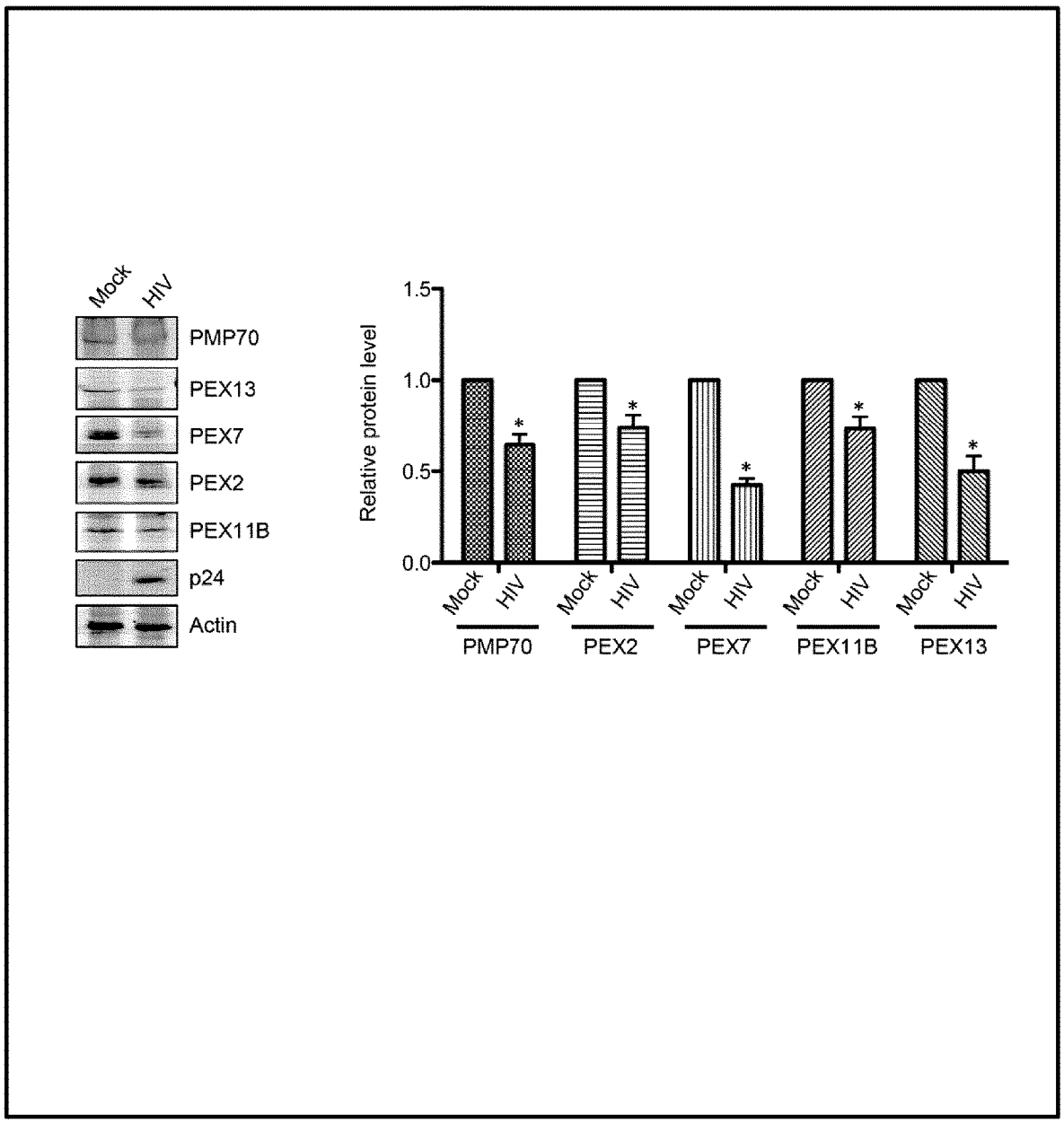
FIG. 14 shows that HIV-1 infection causes loss of peroxisomal proteins in Hela CD4+ cells.

Example 5: HIV-1 Infection Downregulates Peroxisomal Proteins and Decreases Peroxisome Numbers To determine if peroxisomes were affected by HIV-1 infection, immunofluorescence and immunoblot assays were conducted on infected Hela CD4+ cells and monocyte-derived macrophages respectively. Data in FIG. 4, Panel A show that similar to what was observed in miRNA-transfected cells (FIG. 3, Panel B), HIV infection results in significant loss of peroxisomes in Hela CD4+ cells. These cells were used for the microscopy assays because their flat morphology is more conducive for peroxisome quantitation. Peroxisomes were identified using an antibody to the tripeptide Ser-Lys-Leu (SKL), a targeting motif found at the carboxyl termini of many peroxisomal matrix proteins (Gould S J et al. 1989; The Journal of cell biology. 1989; 108(5):1657-64) (FIG. 4, Panel A). Quantification of SKL-positive structures revealed that on average HIV-infected cells contained 40% less peroxisomes than mock-treated cells (FIG. 4, Panel A) Immunoblotting revealed that infection of primary macrophages, a physiologically relevant cell type in HIV patients, also resulted in dramatic loss of PEX2, PEX7, PEX13 and to a lesser extent, PEX11B (FIG. 4, Panel B). However, levels of catalase, a peroxisomal matrix protein were not affected by HIV infection. This indicated that the effects of HIV-1 protein expression on peroxisome-associated proteins were highly specific. Similar results were observed in infected Hela CD4+ cells (FIG. 14).

Figure 5A:
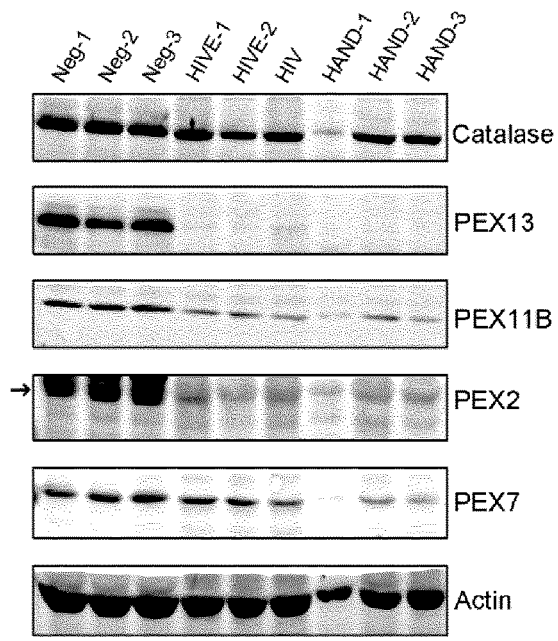
FIGS. 5A and 5B show that HIV-1 infection induces loss of peroxisomal proteins in brain tissue (as determined by immunoblotting).

Next, immunoblotting was used to analyze peroxisomal protein levels and immunohistochemistry to access peroxisome morphology in frontal lobe brain tissue from HIV/AIDS and uninfected patients. Data in FIG. 5A show that PEX13 protein was virtually absent in HIV patients with or without encephalitis or HAND. Levels of PEX7 protein were also significantly (40%) lower in the sample from an HIV patient without encephalitis or HAND, however in three HAND samples, steady state levels of PEX7 protein were lower than those seen in HIV patients without HAND as well as non-infected patients. Finally, levels of PEX2 and PEX11B proteins were reduced (~70-80%) in brain tissue from all of the HIV patients assayed.

Figure 6:
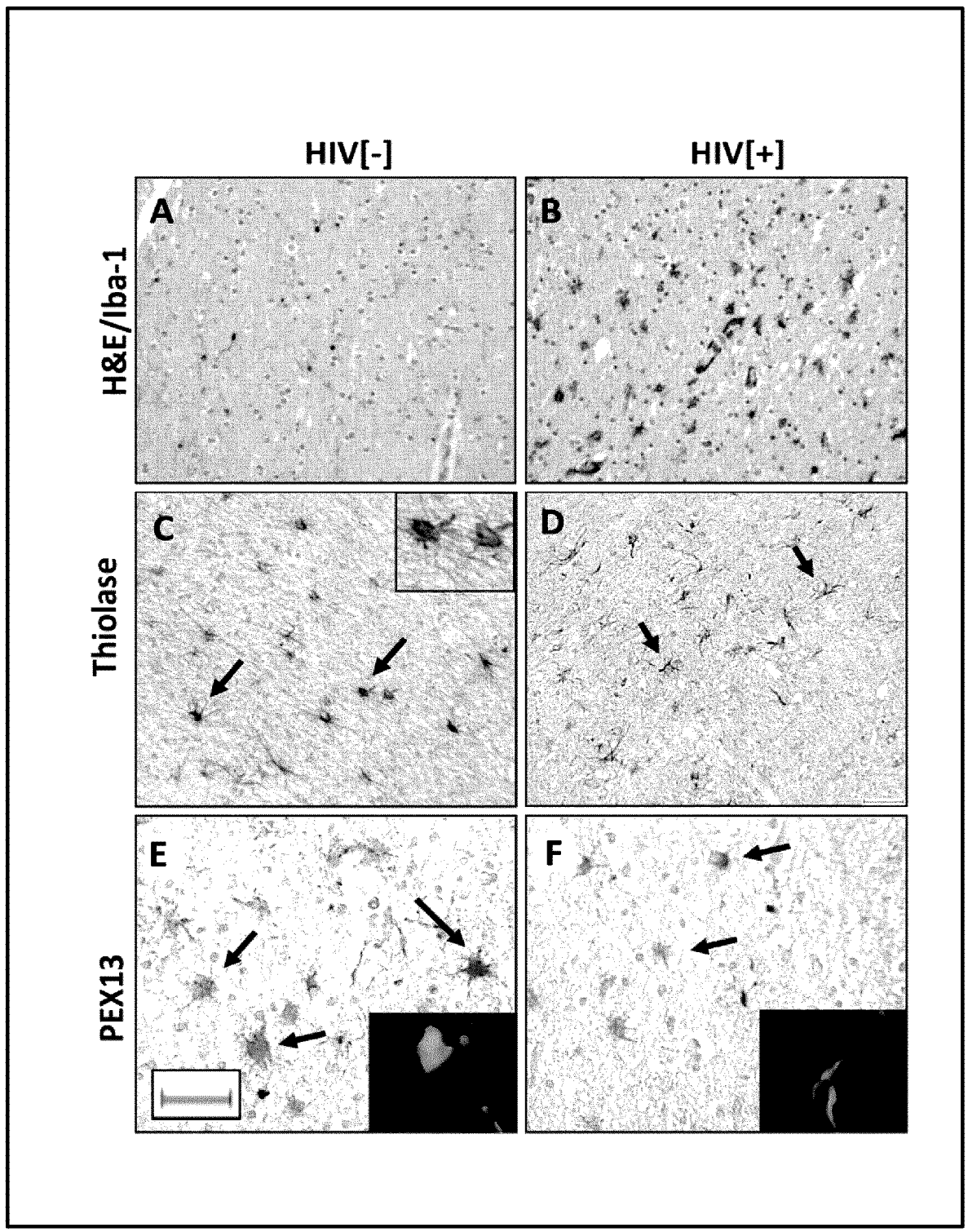
FIG. 6 shows that HIV-1 infection induces loss of peroxisomal proteins in brain tissue (as determined by immunoperoxidase staining).

As a secondary assay, brain tissue from uninfected and HIV/AIDS patients was examined by immunocytochemistry. Immunolabeling of frontal lobe sections showed that the intensity of PEX13 and thiolase immunostaining which was concentrated in astrocytes (arrows), was consistently lower in HIV/AIDS tissue compared to that from uninfected patients (FIG. 6). Although the data are from a small sample size, they suggest that HIV infection contributes to loss of peroxisomal material in brain tissue.

FIG. 4. HIV-1 infection causes loss of peroxisomal proteins and reduces the abundance of peroxisomes. Panel A shows Hela CD4+ cells (clone 1022) were infected with HIV-1 (pYu2, MOI=10.0) for 72 hours and then processed for indirect immunofluorescence and confocal microscopy. Peroxisomes were detected with a rabbit polyclonal antibody to peroxisomal targeting signal SKL and donkey anti-rabbit IgG conjugated to Alexa Fluor 546. HIV-infected cells were detected with a mouse monoclonal antibody to HIV-1 p24 protein and donkey anti-mouse IgG conjugated to Alexa Fluor 488. Nuclei were stained using DAPI. Images were obtained using spinning disc confocal microscopy. The numbers of peroxisomes (SKL-positive structures) in mock- and HIV-infected cells were determined using Volocity image analyses software. Averages were calculated from three independent experiments in which a minimum of 10 cells for each sample were analyzed. The average number in mock-treated cells was normalized to 1.0. Bars represent standard error of the mean. *$p<0.05$. Panel B shows primary monocyte-derived macrophages (MDM) were infected with HIV (pYu2, MOI=2.0) for 5 days and then were subjected to immunoblot analyses with antibodies to Catalase, PEX2, PEX7, PEX11B, PEX13, HIV p24 and actin. The relative levels of peroxisomal proteins (compared to actin) from 3 independent experiments (3 donors) were averaged and plotted. Error bars represent standard error of the mean. *$p<0.05$.

Figure 5B:
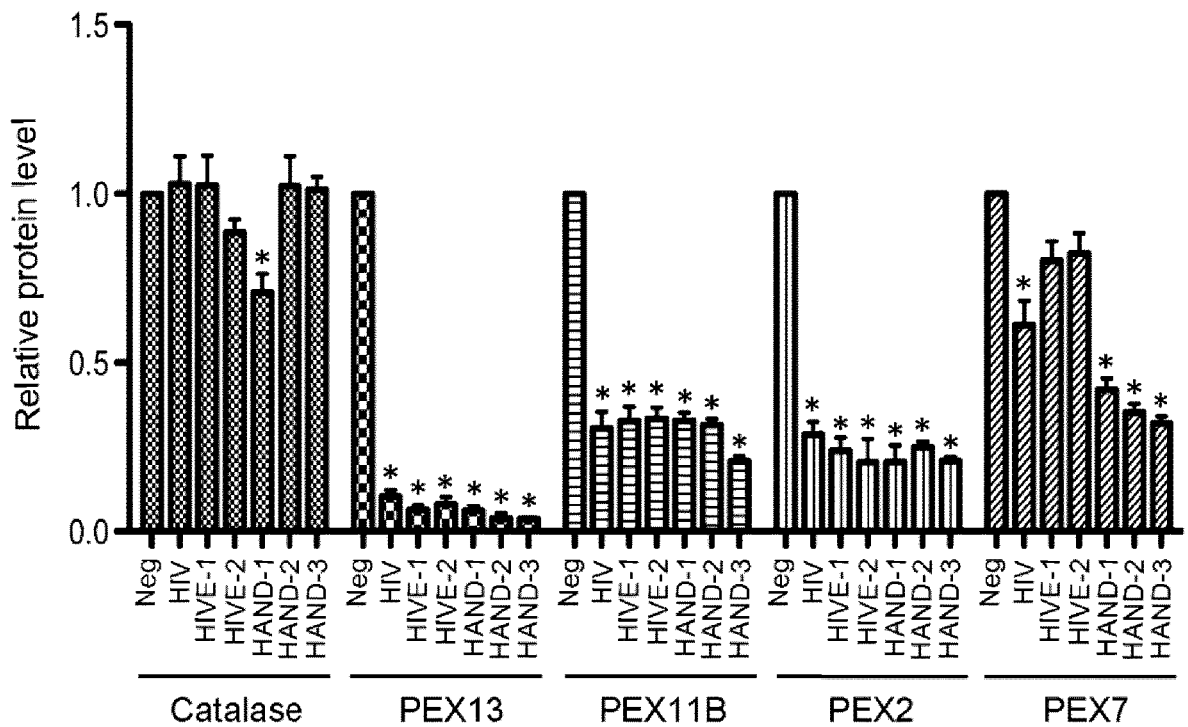

FIGS. 5A and 5B. HIV-1 induces loss of peroxisomal proteins in brain tissue. FIG. 5A shows lysates from brain tissue from HIV negative (Neg-1-3), HIV positive (HIV), HIV positive with encephalitis (HIVE-1-2) and HAND patients (HAND-1-3) were subjected to immunoblotting with antibodies to catalase, PEX2, PEX7, PEX11B, PEX13 and actin. The relative levels of peroxisomal proteins (compared to actin) were averaged and plotted (FIG. 5B). N=3 (triplicate from same sample). Error bars represent standard deviation of the mean. *$p<0.05$.

FIG. 6 shows immunodetection of peroxisome proteins in frontal lobe material from uninfected (HIV[−]) and HIV-infected (HIV[+]) patients. Peroxisomes were labeled with rabbit antibodies PEX13 or thiolase and microglia were detected using rabbit anti-Iba-1. Most of the cells that stain intensely for thiolase and PEX 13 immunopositive cells are astrocytes (arrows) but some could be oligodendrocytes or microglia. Confocal microscopy shows labeled astrocytes (green) and PEX immunoreactivity (scarlet) and DAPI-labeled nuclei. Slides from 4-5 patients per group were reviewed; all HIV+ patients were AIDS-defined and not receiving therapy at the time of death. (Size bar=20 μm).

FIG. 14. HIV-1 infection causes loss of peroxisomal proteins in Hela CD4+ cells. Hela CD4+ cells (clone 1022) were infected with HIV-1 (pYU2, MOI=10.0) for 72 hours and then subjected to immunoblot analyses with antibodies to PMP70, PEX2, PEX7, PEX11B, PEX13, HIV-1 p24 and actin. The relative levels of peroxisomal proteins (compared to actin) from 3 independent experiments were averaged and plotted. Error bars represent standard error of the mean.

Example 6: The Four PEX mRNA Targeting miRNAs are Upregulated During HIV Infection of Macrophages The data in the present study are consistent with a scenario in which the loss of peroxisomes during HIV-1 infection is caused by increased expression of miRNAs that target mRNAs encoding peroxisome biogenesis factors. To address this hypothesis, upregulation of miR-500a-5p, miR-34c-3p, miR-93-3p and/or miR-381-3p were was determined in HIV-infected macrophages. Human primary macrophages were infected with HIV-1 (MOI=2) and after 5 days, relative levels of miRNAs were determined by RT-qPCR. Data in FIG. 7, Panel A show that levels of miR-500a-5p and miR34c-3p were increased almost 2.5 fold whereas miR-93-3p and miR-381p were increased between 1.6 and 2.2 fold. In contrast, levels of miR-483-5p (which does not target PEX mRNAs and was identified as a miRNA whose expression was decreased in brain tissue of HAND patients, FIG. 15A: downregulated miRNAs; FIG. 15B: upregulated miRNAs) were slightly decreased in HIV-infected macrophages.

To further investigate the mechanism underlying HIV-associated loss of peroxisomes, anti-miRs were used to block the functions of PEX mRNA-targeting miRNAs during HIV infection. As transfection of primary macrophages can be technically challenging (Maess M B et al. 2014; J Vis Exp. 2014; (91):e51960), it was elected to employ Hela CD4+ cells for these experiments. Data in FIG. 7, Panel B show that with the exception of miR-93-3p, expression of PEX-targeting miRNAs was significantly elevated in HIV-infected Hela CD4+ cells. Anti-miR-500a-5p had the most effect in that it completely prevented HIV-induced loss of PEX2, PEX7, PEX11B and PEX13 (FIG. 8A). Other miRNA inhibitors had intermediate effects. For example, anti-miR-34c-3p increased levels of PEX13; anti-miR-93-3p increased levels of PEX7 and PEX11B; and anti-miR-381-3p increased levels of PEX11B.

Figure 8A:
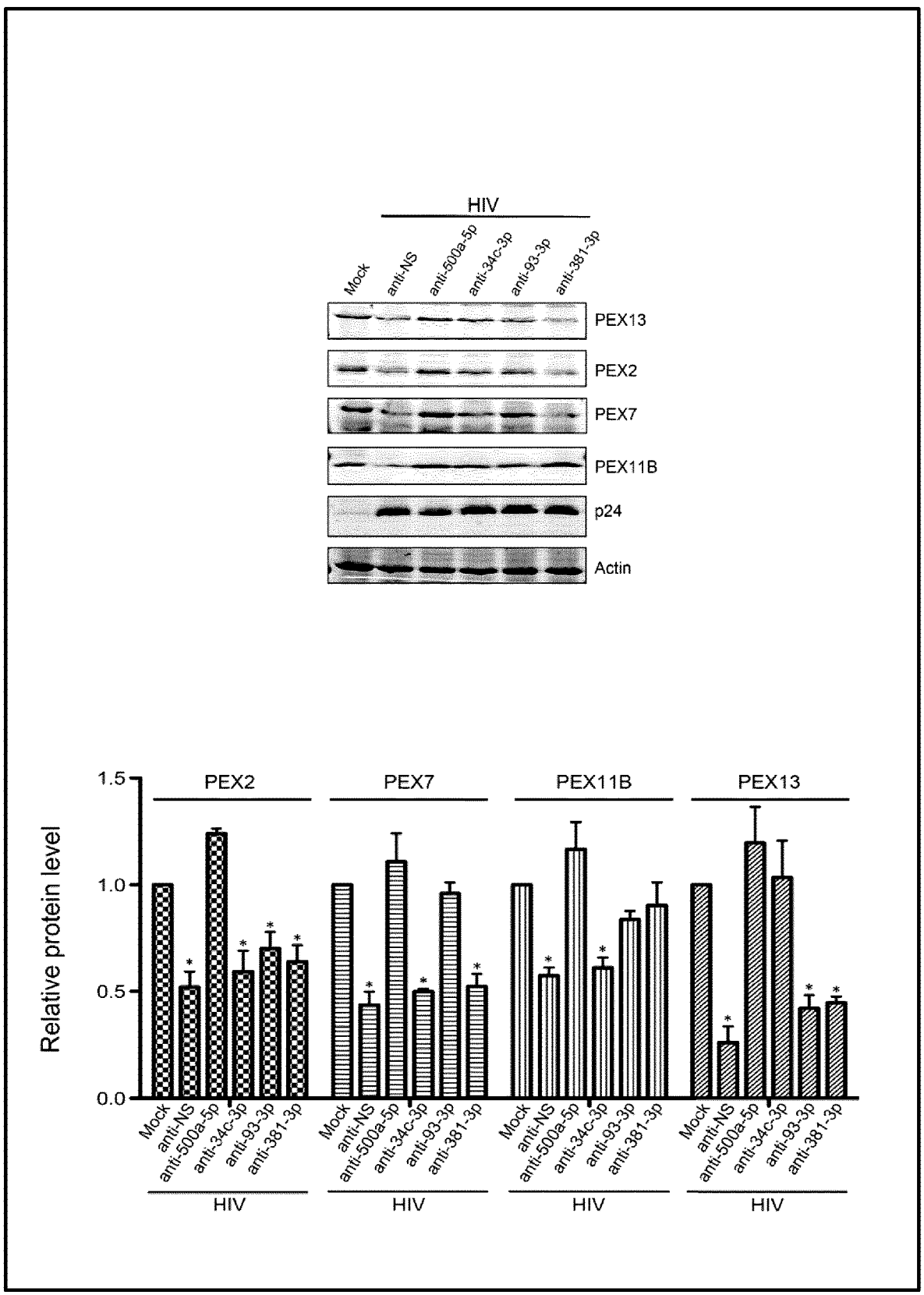
FIG. 8A shows that HIV-induced loss of peroxisomal proteins is abrogated by blocking the function of miR-500a-5p.
Figure 8B:
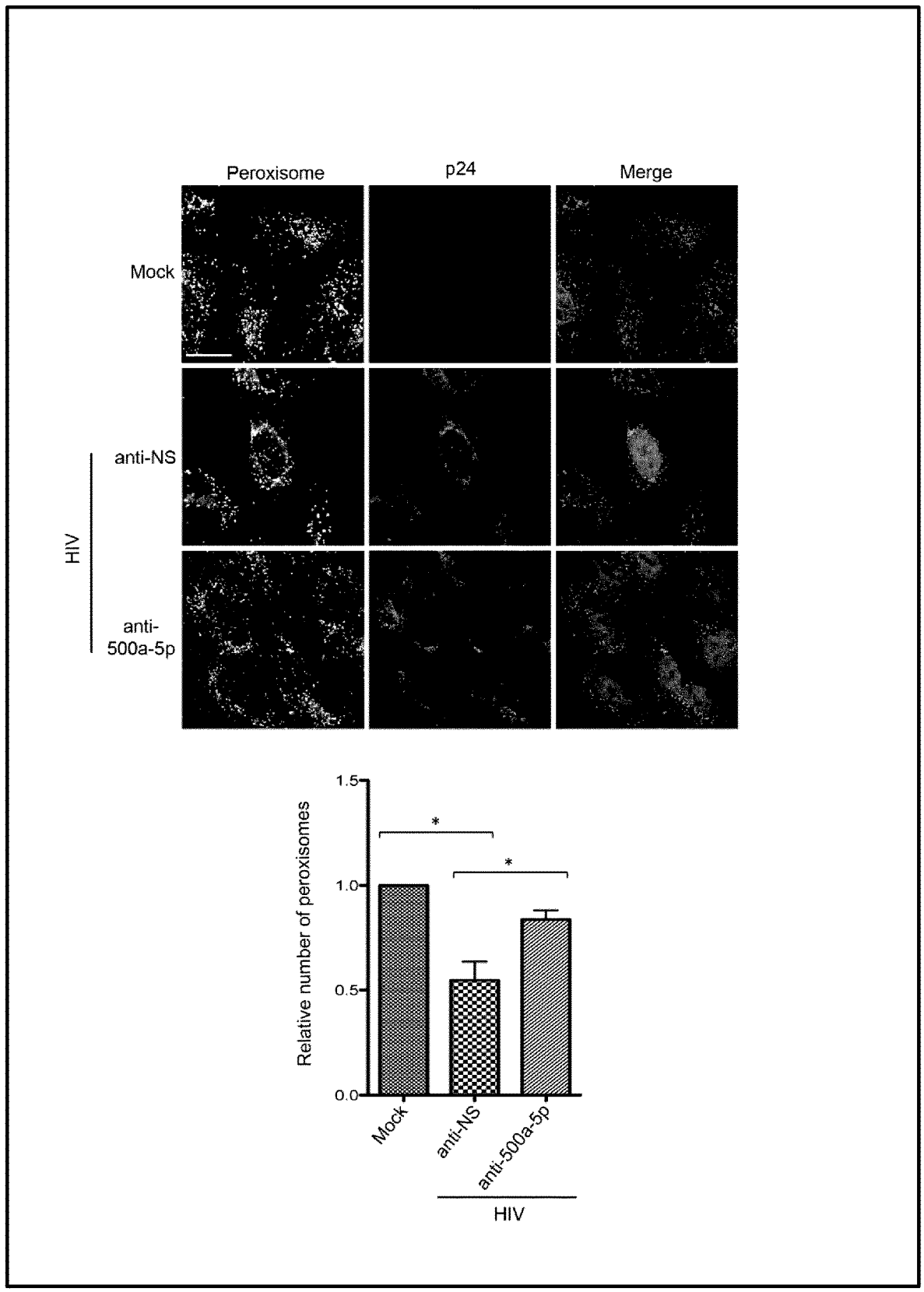
FIG. 8B shows that HIV-induced loss of peroxisomes is abrogated by blocking the function of miR-500a-5p.

Since miR-500a-5p had the greatest effect on peroxisomal protein expression, it was questioned if blocking the activity of this miRNA could prevent HIV-induced loss of peroxisomes. Results in FIG. 8B show that anti-miR-500a-5p abrogated the effect of HIV-1 infection on peroxisomes. Specifically, the average number of peroxisomes in HIV-infected cells containing the inhibitor of miR-500a-5p was not statistically different from that of mock-treated cells.

Figure 7:
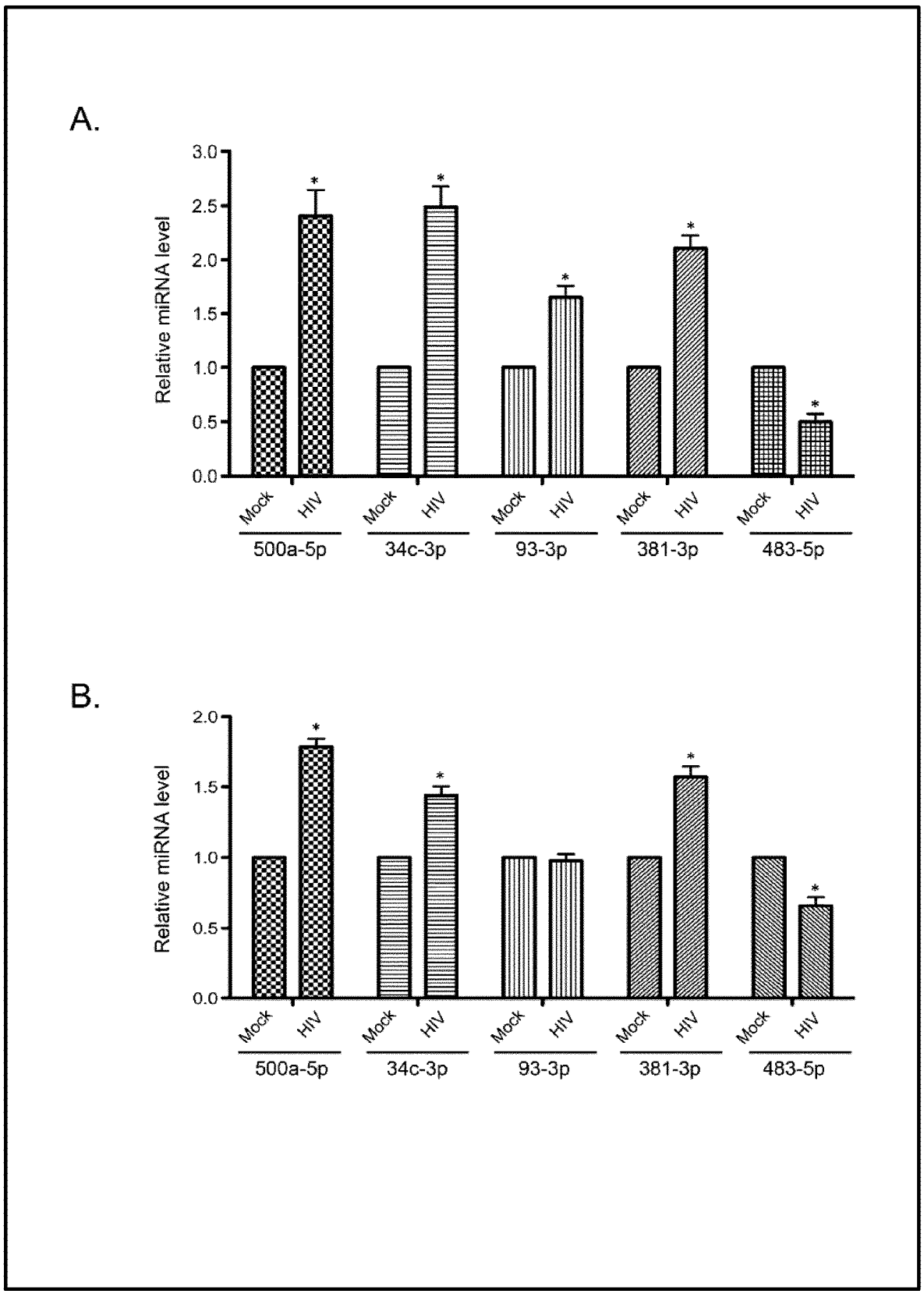
FIG. 7 shows that HIV-1 infection of primary human macrophages (A) and Hela CD4+ cells (B) upregulates expression level of multiple miRNAs that target PEX mRNAs (panels A and B).

FIG. 7. HIV-1 infection upregulates expression level of multiple miRNAs that target PEX mRNAs. Panel A shows primary monocyte-derived macrophages (MDM) from 3 donors were infected with HIV (pYu2, MOI=2.0) for 5 days and relative levels of miRNAs were determined by RT-PCR from total RNA extracted from the samples. The average relative levels of miRNAs (normalized to snRNU6) from 3 independent experiments were determined. Error bars represent standard error of the mean. Panel B shows Hela CD4+ cells were infected with HIV-1 (pYu2, MOI=10.0) for 48 hours and relative levels of miRNAs were determined as described in panel A. N=3. Error bars represent standard error of the mean. *$p<0.05$.

FIG. 8. HIV-induced loss of peroxisomal proteins and peroxisomes is abrogated by blocking the function of miR-500a-5p. FIG. 8A shows HEK293T cells were transfected with a plasmid encoding HIV-1 provirus (pYU2) for 12 hours after which cells were transfected with anti-miRs that are complementary to the HAND-associated PEX-specific miRNAs. Cell lysates were collected 36 hours later and then subjected to immunoblot analyses with antibodies to PEX2, PEX7, PEX11B, PEX13, HIV-1 p24 and actin. The relative levels of peroxisomal proteins (normalized to actin) from 3 independent experiments were determined. Error bars represent standard error of the mean. *$p<0.05$. FIG. 8B shows Hela CD4+ cells (clone 1022) were infected with HIV-1 (MOI=10) for 16 hours and then transfected with anti-miR-500a-5p. Forty-eight hours later, cells were processed for indirect immunofluorescence and confocal microscopy. Peroxisomes were detected with a rabbit polyclonal antibody to the peroxisomal targeting signal SKL and donkey anti-rabbit IgG conjugated to Alexa Fluor 488. HIV-infected cells was detected with a mouse monoclonal antibody to HIV-1 p24 and donkey anti-mouse IgG conjugated to Alexa Fluor 546. Nuclei were stained using DAPI. Images were obtained using spinning disc confocal microscopy. Size bar is 10 μM. The relative numbers of peroxisomes (SKL-positive structures) in mock and HIV-infected cells transfected with or without anti-miR-500a-5p were determined using Volocity image analyses software. The average numbers of peroxisomes/cell were calculated from three independent experiments in which a minimum of 10 cells for each sample were analyzed. *p<0.05.

FIGS. 15A-15B shows a list of potential target genes of differentially expressed miRNAs in brains of HAND compared to nonHAND patients by computational prediction. Three bioinformatics algorithms (TargetScan, miRDB and DIANA) were used to predict targets of each miRNA and those high-ranking potential targets predicted by at least two out of three algorithms were listed. Down-regulated and up-regulated miRNAs are listed in FIG. 15A and FIG. 15B, respectively. Notably, peroxisomal genes (PEX2, PEX7, PEX11B and PEX13) that were predicted the potential targets of 4 up-regulated miRNAs (miR-500a-5p, miR-34c-3p, miR-93-3p, and miR-381-3p) were highlighted.

Figure 9:
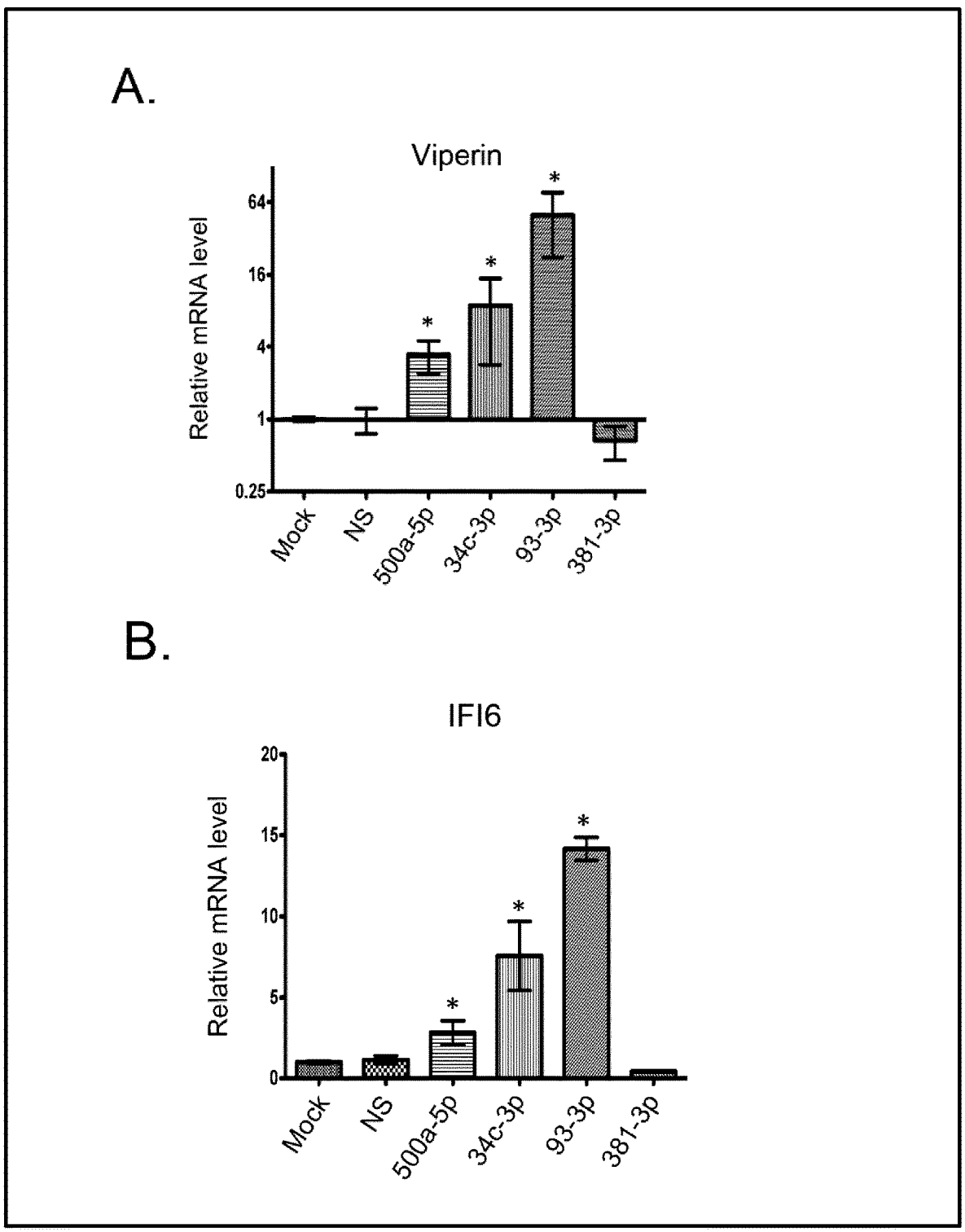
FIG. 9 shows that transfection of miRNA mimics that target PEX mRNAs leads to increased levels of innate immune mRNAs encoding viperin (panel A) and IFI6 (panel B).
Figure 11:
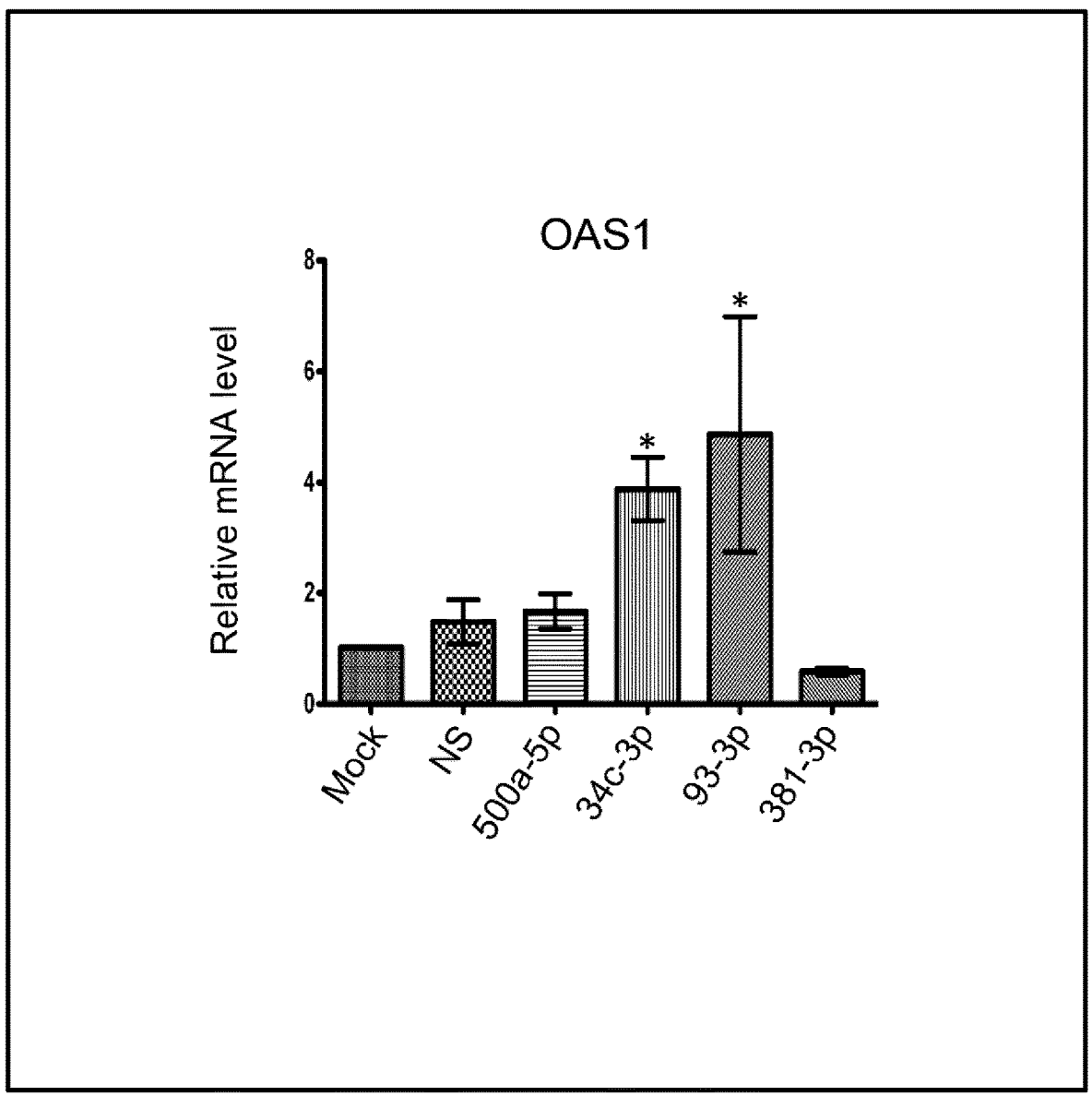
FIG. 11 shows that transfection of miRNA mimics that target PEX mRNAs leads to increased levels of innate immune mRNAs encoding OAS1.

Example 7: Some HIV-Induced miRNAs that Target PEX mRNAs Enhance Expression of Innate Immune Genes Because peroxisomes are more recently recognized to have important roles in antiviral signaling (Dixit E et al. 2010; Cell. 2010; 141(4):668-81; Odendall C et al. 2014; Nature immunology. 2014; 15(8):717-26), it was questioned if expression of miRNA mimics that target PEX mRNAs would affect innate immune genes. A549 cells were chosen for these experiments because they were human in origin and have been used extensively to study innate immune signaling. Interestingly, three of the miRNA mimics (miR-500a-5p, miR-34c-3p and miR-93-3p) significantly increased mRNA levels for five innate immune genes (FIGS. 9-11). MiR-93-3p had the most dramatic affect on expression of antiviral genes. Specifically, in cells transfected with miR-93-3p mimic, expression of IFI6 and viperin mRNAs were increased 14-fold and 50-fold respectively. MiR-500a-5p appeared to modestly increase expression of innate immune genes (2-4 fold) whereas miR-381-3p did not significantly affect expression of viperin, IFI6, IFIT2, IRF1 or OAS1 (FIGS. 9-11).

The present study found that of the 17 miRNAs whose expression levels were commonly deregulated in HAND patients, four (miR-500a-5p, miR-34c-3p, miR-93-3p, and miR-381-3p) were shown to regulate expression of the peroxisome biogenesis factors PEX2, PEX7, PEX11B and PEX13. Subsequent analyses revealed that elevated expression of these miRNAs was not specific to HIV-HAND but rather, was a common feature of HIV infection. This demonstrated that viral infection lead to increased expression of miRNAs that downregulate peroxisomes.

FIGS. 9-11. Transfection of miRNA mimics that target PEX mRNAs leads to increased levels of innate immune mRNAs. A549 cells were transfected with miRNA mimics (30 nM) for miR-NS, miR-500a-5p, miR-34c-3p, miR-93-3p or miR-381-3p. Forty-eight hours later, total RNA was extracted from the cells for use in RT-PCR. Relative levels of innate immune mRNAs (Viperin (FIG. 9, Panel A), IFI6 (FIG. 9, Panel B), IFIT2 (FIG. 10, Panel A), IRF1 (FIG. 10, Panel B), and OAS1 (FIG. 11)) from 3 independent experiments were determined by RT-PCR from total RNA extracted from the samples. Error bars represent standard error of the mean.

Example 8: Niclosamide Increases PEX7 Expression and Inhibits HIV Replication

HeLa CD4+ cells were pretreated with the indicated concentrations of the peroxisome proliferator, niclosamide for 24 hrs or DMSO alone (vehicle control). Cells were then infected with HIV, MOI=0.5) for 48 hrs after which levels of the viral protein p24 were measured by ELISA. Niclosamide significantly inhibited HIV replication. See FIG. 17.

Figure 18:
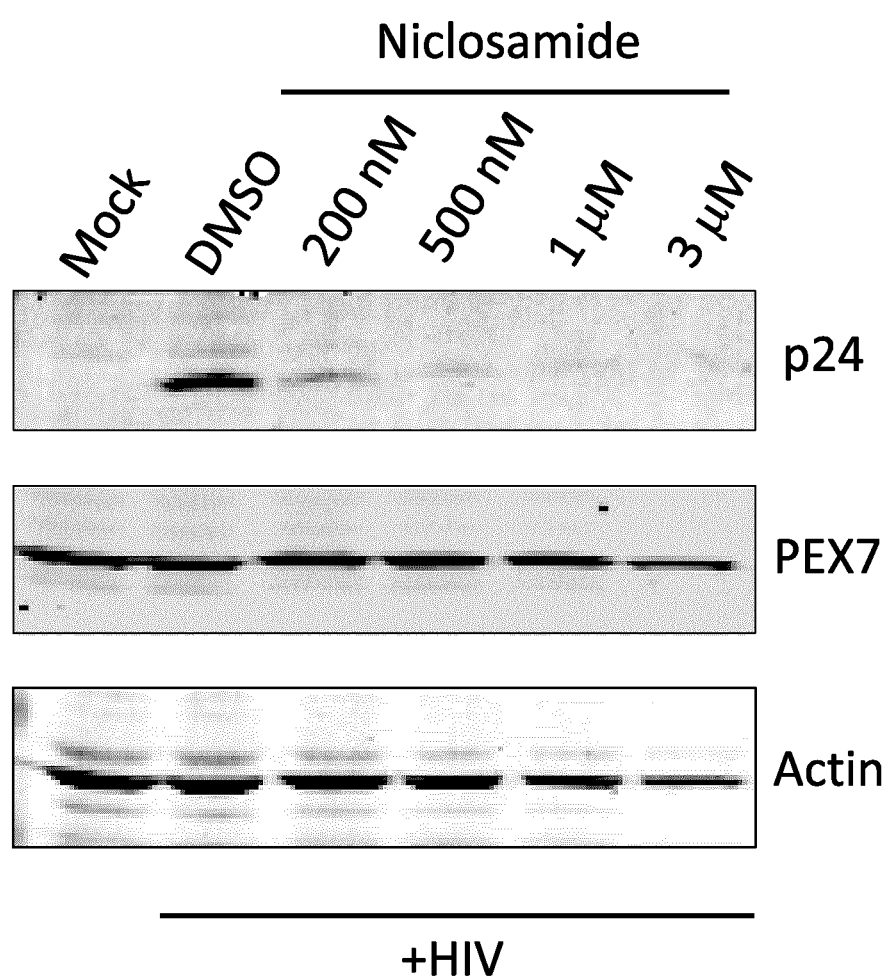
FIG. 18 shows that niclosamide inhibits expression of HIV p24 protein.

HeLa CD4+ cells were pretreated with the indicated concentrations of the peroxisome proliferator, niclosamide for 24 hrs or DMSO alone (vehicle control). Cells were then infected with HIV, MOI=0.5) for 48 hrs after which levels of the viral protein p24 and peroxisomal protein were measured by immunoblotting. Actin served as loading control. Niclosamide inhibited expression of HIV p24 protein. See FIG. 18.

Figure 19:
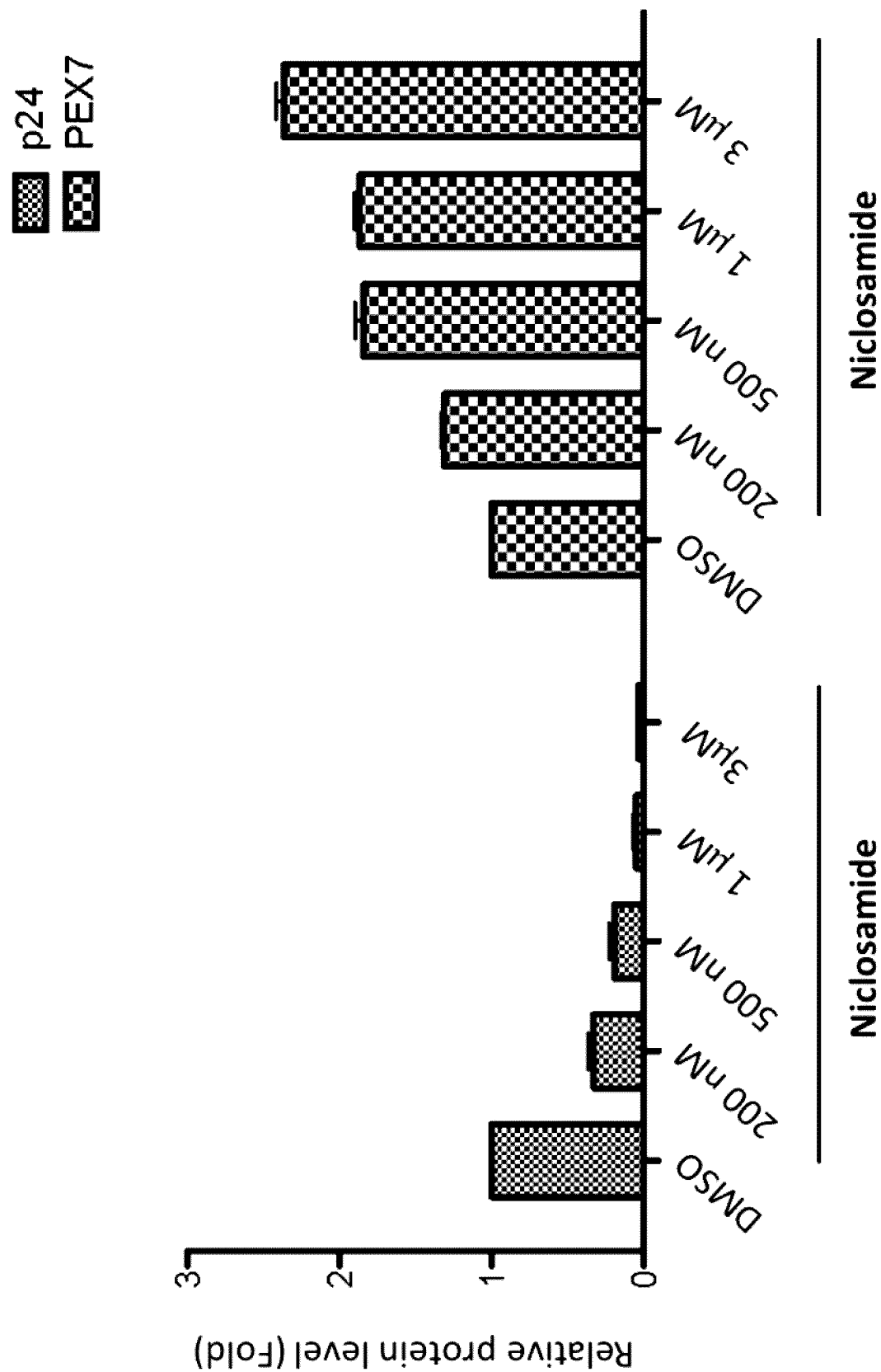
FIG. 19 shows that niclosamide increases expression of the peroxisomal protein PEX7 and inhibits HIV replication.

FIG. 19 shows quantitation of relative (to DMSO-treated cells) p24 and PEX7 protein levels in HIV-infected HeLa CD4+ cells after 48 hrs. Niclosamide increased expression of the peroxisomal protein PEX7 and inhibited HIV replication.

Figure 20:
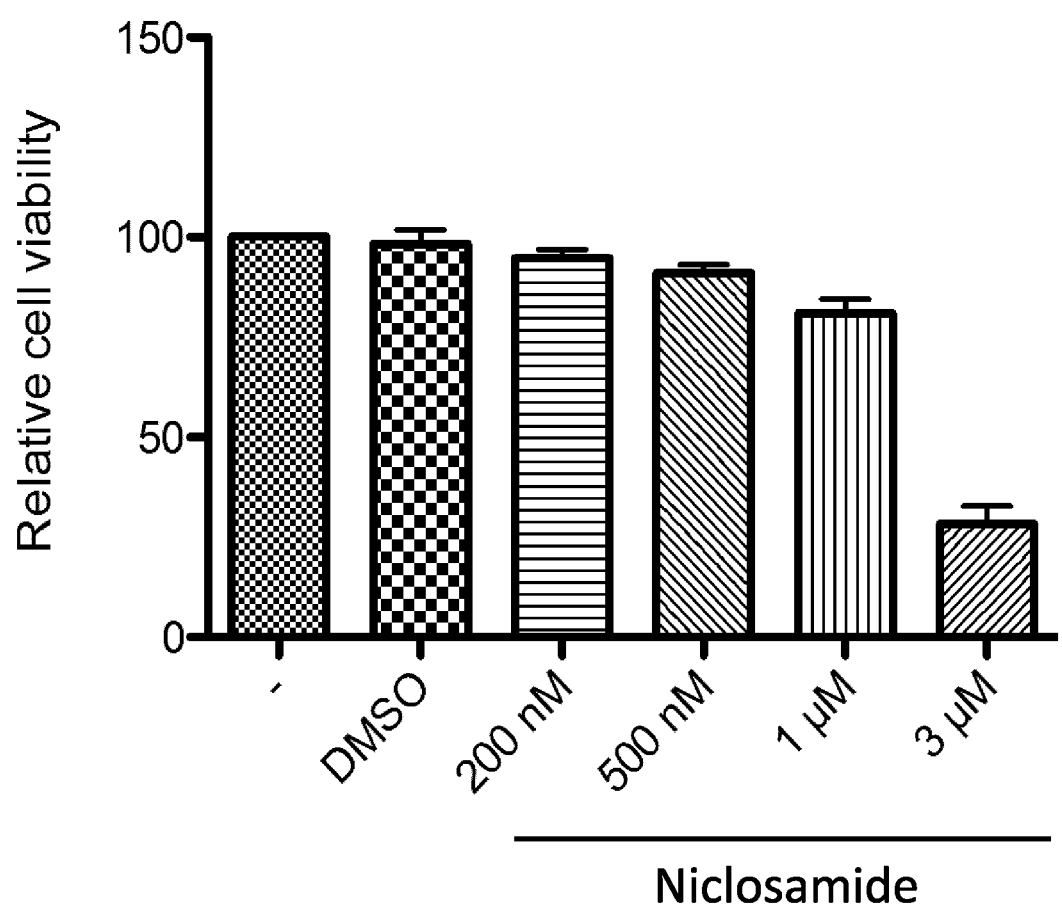
FIG. 20. Viability of niclosamide-treated cells.

Cells treated with niclosamide or DMSO were harvested after 72 hours. Relative cell viability was determined by measuring ATP levels in the cell lysates. Below 1 micromolar, niclosamide is not cytotoxic. See FIG. 20.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of treating a HIV patient diagnosed as having an increased risk for developing human immunodeficiency virus (HIV)-associated neurocognitive disorder (HAND), the method comprising:

administering a peroxisome proliferator comprising 5-chloro-N-(2-chloro-4-nitrophenyl)-2-hydroxybenzamide (CAS No. 50-65-7), or a pharmaceutically acceptable salt, solvate, clathrate, hydrate or polymorph thereof, or fenofibrate or a derivative or salt thereof, to the patient in an amount effective to treat HIV, wherein the HIV patient has been diagnosed as having an increased risk for developing HAND by:

(i) detecting an increased level of miR-500a-5p, miR-34c-3p, miR-93-3p, and/or miR-381-3p relative to a control; or (ii) detecting a decreased level of a peroxin selected from the group consisting of PEX2, PEX19, PEX7, PEX11B, and PEX13, relative to a control.

2. The method of claim 1, wherein the HIV patient has also been diagnosed as having an increased risk for developing HAND based upon increased level of a substrate for peroxisomal enzyme.

3. The method of claim 2, wherein the substrate comprises a long chain fatty acid comprising 14-21 carbon atoms.

4. The method of claim 2, wherein the substrate comprises a very long chain fatty acid comprising 22-26 carbon atoms.

* * * * *